US012336470B2

(12) United States Patent
Berentsen et al.

(10) Patent No.: US 12,336,470 B2
(45) Date of Patent: Jun. 24, 2025

(54) METHOD FOR SELECTING SEED SIZE IN WATERMELON AND GENERATING MODIFICATIONS IN THE TOMATO-SEED SIZE GENE

(71) Applicant: NUNHEMS B.V., Nunhem (NL)

(72) Inventors: Richard Bernard Berentsen, Paterna (ES); Courtney Hu, Sacramento, CA (US); Elena Chiapparino, Sant Agata Bolognese Emilia-Romagna (IT)

(73) Assignee: NUNHEMS B.V., Nunhem (NL)

( * ) Notice: Subject to any disclaimer, the term of this patent is extended or adjusted under 35 U.S.C. 154(b) by 205 days.

(21) Appl. No.: 17/800,388

(22) PCT Filed: Feb. 9, 2021

(86) PCT No.: PCT/EP2021/053032
§ 371 (c)(1),
(2) Date: Aug. 17, 2022

(87) PCT Pub. No.: WO2021/165091
PCT Pub. Date: Aug. 26, 2021

(65) Prior Publication Data
US 2023/0092854 A1    Mar. 23, 2023

Related U.S. Application Data

(60) Provisional application No. 62/977,834, filed on Feb. 18, 2020.

(51) Int. Cl.
| | |
|---|---|
| *A01H 1/04* | (2006.01) |
| *A01H 5/10* | (2018.01) |
| *A01H 6/34* | (2018.01) |

(52) U.S. Cl.
CPC .............. *A01H 1/045* (2021.01); *A01H 5/10* (2013.01); *A01H 6/342* (2018.05)

(58) Field of Classification Search
None
See application file for complete search history.

(56) References Cited

U.S. PATENT DOCUMENTS

| | | | |
|---|---|---|---|
| 7,550,652 B2 | 6/2009 | Zhang | |
| 9,763,399 B2 | 9/2017 | De et al. | |
| 2020/0093086 A1 | 3/2020 | De Groot et al. | |

FOREIGN PATENT DOCUMENTS

| | | |
|---|---|---|
| CN | 105713971 A | 6/2016 |
| CN | 110904264 A | 3/2020 |
| KR | 20170045848 A | 4/2017 |

OTHER PUBLICATIONS

Allen, et al., "Transcript-specific, single-nucleotide polymorphism discovery and linkage analysis in hexaploid bread wheat (*Triticum aestivum* L.)", Plant biotechnology Journal, vol. 9, Issue 9, Jun. 1, 2011, pp. 1086-1099.
Henikoff, et al., "Amino acid substitution matrices from protein blocks", Proceedings of the National Academy of Sciences, vol. 89, Issue 22, Nov. 15, 1992, pp. 10915-10919.
International Search Report for PCT Patent Application No. PCT/EP2021/053032, Issued on Jun. 23, 2021, 4 pages.
Jiannong Zhang, et al., "Breeding and production of watermelon for edible seed in China", Cucurbit Genetics Cooperative Report, vol. 19, Jul. 11, 1996, pp. 66-67.
Kim, et al., "Major Quantitative Trait Loci and Putative Candidate Genes for Powdery Mildew Resistance and Fruit-Related Traits Revealed by an Intraspecific Genetic Map for Watermelon (*Citrullus lanatus* var. *lanatus*)", Plos One, vol. 10, Issue 12, Dec. 23, 2015, 18 pages.
Li, et al., "Fine mapping and discovery of candidate genes for seed size in watermelon by genome survey sequencing", Scientific Reports, vol. 8, Article No. 17843, Dec. 14, 2018, 11 pages.
Liu, et al., "Targeted deletion of floral development genes in *Arabidopsis* with CRISPR/Cas9 using the RNA endoribonuclease Csy4 processing system", Horticulture research, vol. 6, Aug. 21, 2019, 10 pages.
McCallum, et al., "Targeting Induced Local Lesions IN Genomes (TILLING) for plant functional genomics", Plant physiology, vol. 123, Issue 2, Jun. 2000, pp. 439-442.
Rodriguez-Leal, et al., "Engineering quantitative trait variation for crop improvement by genome editing", Cell, vol. 171, Issue 2, Oct. 5, 2017, pp. 470-480.
Todd C Wehner, "Gene list for watermelon, 2007", Cucurbit Genetics Cooperative Report, vol. 30, 2007, pp. 96-120.
Zhang, et al., "Tissue culture-induced heritable genomic variation in rice, and their phenotypic implications", PloS one, vol. 9, Issue 5, May 7, 2014, pp. 1-10.

*Primary Examiner* — Brent T Page
(74) *Attorney, Agent, or Firm* — ArentFox Schiff LLP

(57) ABSTRACT

The disclosure provides methods for selecting watermelon plants for genetic elements on chromosome 2 and 6 which genetic elements predict the average seed size produced in the fruits of said plants and watermelon plants and plant parts comprising modifications in the tomato-seed size gene (Ts-gene) on chromosome 2, and methods of producing seeds and plants.

9 Claims, 7 Drawing Sheets
Specification includes a Sequence Listing.

Figure 1

```
  1 MGFKGFVIRSYEESQLSDKAQVMDLERRCEIGQSKRVFLFTDTLGDPICR      50
 51 IRNSPMYKMLVAERDKEVVGVIQGSIKPVFFTAHKPPPGLVVKLGYILGL     100
101 RVAPPYRRRGIGSSLVRRLEDWFLSNDVDYCCMATEKDNHASLNLFINNL     150
151 RYIKFRTGRILVNPVRNHPYNMNSSEINIQKLKIEEAEAIYKKHMASTEF     200
201 FPKDIKNILKNKLSLGTWVANFKQPPWSSSNSVGGNGQTMASSWAIVSLW     250
251 NSGEVFKLRLGKAPFPWLIYTKSLKIMDKIFPCFKVVLVPNFFKPFGFYF     300
301 VYGLHHEGPFSERLVGALCKFVHNMALNNSKDNCKAIVTEIGGDEDDGLK     350
351 MEIPHWKLLSCYEDFWCIKSLKSKRYNNISNDNDNDNDHDHHILEWTNAS     400
401 PNRTLFVDPREV  412
```

Figure 2

| Three genotypes on chromosome 2 for the Ts protein (homozygous) | Chromosome 2 seed size haplotype | SNP_01 marker genotype on chromosome 6 (homozygous) | INDEL_02 marker genotype on chromosome 6 (homozygous) (D is deletion) (I is insertion / no deletion) | Chromosome 6 seed size haplotype S = Small M = Medium L = Large | index | Predicted Seed size and weight of the seeds in the fruits, g/10 seeds | Predicted Seed size and weight of the seeds in the fruits, g/10 seeds (range) |
|---|---|---|---|---|---|---|---|
| no function (NO/NO) | NO | G/G (SEQ ID NO: 4 / SEQ ID NO: 4) | D/D (SEQ ID NO: 6 / SEQ ID NO: 6) | S | 1 | 0.07 | Small seed size (0.07 – 0.26) |
| no function (NO/NO) | NO | G/G (SEQ ID NO: 4 / SEQ ID NO: 4) | I/I (SEQ ID NO: 7 / SEQ ID NO: 7) | M | 2 | 0.13 | |
| no function (NO/NO) | NO | T/T (SEQ ID NO: 5 / SEQ ID NO: 5) | D/D (SEQ ID NO: 6 / SEQ ID NO: 6) | M | 2 | 0.13 | |
| no function (NO/NO) | NO | T/T (SEQ ID NO: 5 / SEQ ID NO: 5) | I/I (SEQ ID NO: 7 / SEQ ID NO: 7) | L | 3 | 0.26 | |
| Reduced function (RE/RE) | RE | G/G (SEQ ID NO: 4 / SEQ ID NO: 4) | D/D (SEQ ID NO: 6 / SEQ ID NO: 6) | S | 4 | 0.15 | Medium seeds size (0.15 - 0.61) |
| Reduced function (RE/RE) | RE | G/G (SEQ ID NO: 4 / SEQ ID NO: 4) | I/I (SEQ ID NO: 7 / SEQ ID NO: 7) | M | 5 | 0.30 | |
| Reduced function (RE/RE) | RE | T/T (SEQ ID NO: 5 / SEQ ID NO: 5) | D/D (SEQ ID NO: 6 / SEQ ID NO: 6) | M | 5 | 0.30 | |
| Reduced function (RE/RE) | RE | T/T (SEQ ID NO: 5 / SEQ ID NO: 5) | I/I (SEQ ID NO: 7 / SEQ ID NO: 7) | L | 6 | 0.61 | |
| Wild type / functional (WT/WT) | WT | G/G (SEQ ID NO: 4 / SEQ ID NO: 4) | D/D (SEQ ID NO: 6 / SEQ ID NO: 6) | S | 7 | 0.27 | Large seed size (0.27 - 0.97) |
| Wild type / functional (WT/WT) | WT | G/G (SEQ ID NO: 4 / SEQ ID NO: 4) | I/I (SEQ ID NO: 7 / SEQ ID NO: 7) | M | 8 | 0.41 | |
| Wild type / functional (WT/WT) | WT | T/T (SEQ ID NO: 5 / SEQ ID NO: 5) | D/D (SEQ ID NO: 6 / SEQ ID NO: 6) | M | 8 | 0.41 | |
| Wild type / functional (WT/WT) | WT | T/T (SEQ ID NO: 5 / SEQ ID NO: 5) | I/I (SEQ ID NO: 7 / SEQ ID NO: 7) | L | 9 | 0.97 | |

Figure 3

|  |  |  |  | P1 | P1 | P1 | P1 | P1 | P1 | P1 | P1 | P1 |
|---|---|---|---|---|---|---|---|---|---|---|---|---|
|  |  |  | P1 index | 1 | 2 | 3 | 4 | 5 | 6 | 7 | 8 | 9 |
|  |  |  | Chr2 | NO | NO | NO | RE | RE | RE | WT | WT | WT |
|  | P2 index | Chr2 | Chr6 | S | M | L | S | M | L | S | M | L |
| P2 | 1 | NO | S | 0.07 |  |  |  |  |  |  |  |  |
| P2 | 2 | NO | M | 0.08 | 0.13 |  |  |  |  |  |  |  |
| P2 | 3 | NO | L | 0.08 | 0.16 | 0.26 |  |  |  |  |  |  |
| P2 | 4 | RE | S | 0.14 | 0.15 | 0.18 | 0.15 |  |  |  |  |  |
| P2 | 5 | RE | M | 0.20 | 0.28 | 0.28 | 0.16 | 0.30 |  |  |  |  |
| P2 | 6 | RE | L | 0.24 | 0.34 | 0.55 | 0.18 | 0.35 | 0.61 |  |  |  |
| P2 | 7 | WT | S | 0.22 | 0.24 | 0.29 | 0.20 | 0.29 | 0.30 | 0.27 |  |  |
| P2 | 8 | WT | M | 0.29 | 0.38 | 0.40 | 0.29 | 0.40 | 0.55 | 0.28 | 0.41 |  |
| P2 | 9 | WT | L | 0.35 | 0.76 | 0.90 | 0.30 | 0.50 | 0.90 | 0.29 | 0.55 | 0.97 |

METHOD FOR SELECTING SEED SIZE IN WATERMELON AND GENERATING MODIFICATIONS IN THE TOMATO-SEED SIZE GENE

CROSS-REFERENCE TO RELATED APPLICATIONS

This application is a National Stage Entry of PCT/EP2021/053032, filed Feb. 9, 2021, which claims priority to U.S. Provisional Application No. 62/977,834, filed Feb. 18, 2020, the disclosures of each of which are hereby incorporated by reference in their entirety.

BACKGROUND

Zhang describes in Cucurbit Genetics Cooperative Report 19:66-67 (1996) a cross between a "tomato seed size mutant" ("ts" or "tss", from the tomato seed Sugar Baby mutant plant) with GN-1 having edible seeds. Zhang found that seed length and width were controlled by a single gene with two alleles, and incomplete dominance between the alleles. This is-gene mutant is also described in Wehner (2007, Cucurbit Genetic Cooperative Report 30:96-120, Gene List for Watermelon). Wehner describes that there are four genes involved in seed length. Genes(s) for short seed length, (1) for long seed length, whereby LL SS gives medium length, 11 SS gives long length and LL ss or ll ss gives short length; the Ti gene for tiny seed, and the is gene which gives seeds shorter and narrower than the short seeds (11 ss). The tomato seed mutant is mentioned to have the genotype LL ss tsts (also written as L/L s/s ts/ts).

None of these genes are, however, known to date. Nor is it known if or how these genes interact with other genes or loci.

SUMMARY OF VARIOUS ASPECTS OF THE DISCLOSURE

Small seed size is a desired characteristic in watermelon fruit production to make the fruits attractive for consumers and it eliminates the need to produce triploid, seedless watermelon fruits. The production of triploid seedless watermelons is very time consuming and costly, as first stable diploid and tetraploid parent lines have to be produced and triploid fruit production requires a lot of space in the field due to the need for interplanting pollinizer plants to initiate fruit formation. As such, an object of this disclosure is to understand the genetic basis for selecting watermelon plants that produce fruits of certain seed sizes, especially which produce medium or small seed sizes, rather than large seed sizes.

The disclosure relates to the field of watermelon breeding, especially to a method for selecting combinations of genotypes at three loci, one on chromosome 2 and the other two on chromosome 6, which together determine seed size in watermelon. For the locus on chromosome 2, three haplotypes have been identified, and for the two loci on chromosome 6 three haplotypes have been also identified, whereby nine different combinations of haplotypes can be selected for.

DETAILED DESCRIPTION

It was found that the three haplotypes on chromosome 2 in watermelon are determined by the functionality of a protein called the Ts-protein (encoded by the Ts-gene), whereby either the Ts-allele is deleted or mutated so that no functional Ts-protein is present in the plant (e.g., due to a mutation in the promoter preventing expression or mutations leading to a loss-of-function protein being produced), or the ts-allele is mutated so that a reduced function Ts-protein is present or a reduced level of wild type Ts-protein is being made, or a wild type Ts-allele is present producing a functional Ts-protein. These three chromosome 2 haplotypes are indicated herein as 'NO' for 'no functional Ts-protein', 'RE' for 'reduced function Ts-protein' and 'WT' for 'wild type, functional Ts-protein'. Haplotype NO has small seed size, haplotype RE has a medium seed size and haplotype WT has large seed size.

These three chromosome 2 haplotypes (NO, RE and WT) interact with three chromosome 6 haplotypes, indicated as 'S' for 'small seed size', 'M' for 'medium seed size' and for 'large seed size'. For inbred lines (homozygous for the haplotypes), nine combinations of these haplotypes are possible, as shown in FIG. 2.

Plants which have the haplotype 'NO' on chromosome 2 will make small seeds in their fruits, but the average seed size (expressed as grams per 10 seeds) will depend on whether the chromosome 6 haplotype of the plant is S, M or L. Plants having haplotype 'RE' on chromosome 2 will make medium size seeds in their fruits, but the average seed size (expressed as grams per 10 seeds) will depend on whether the chromosome 6 haplotype of the plant is S, M or L. And plants having haplotype 'WT' on chromosome 2 will make large size seeds in their fruits, but the average seed size (expressed as grams per 10 seeds) will again depend on whether the chromosome 6 haplotype of the plant is S, M or L.

The chromosome 2 and chromosome 6 haplotype information can, therefore, be used to generate and/or select inbred lines which develop seeds in their fruits of a predicted seed size. Likewise, the chromosome 2 and chromosome 6 haplotype information can be used to select inbred parent lines to generate F1 hybrids, which develop seeds in their fruits of a predicted seed size. The correlation between the predicted seed size and the actual seed size was found to be high for both inbred lines and for F1 hybrids made from selected inbred lines, especially for small seed size and medium seeds size. As diploid seeds having small seeds are highly desired by consumers, the haplotype information enables the breeder to develop watermelon fruits with small or medium seed size, by selecting plant lines having the haplotype which results in such small or medium seeds sizes. Likewise, large seed size can be selected if desired.

The disclosure enables the skilled person to generate modifications in the allele found at the Ts-gene locus on chromosome 2, i.e., in the "tomato-seed size" gene (Ts-gene), and to generate watermelon plants, seeds and plant parts comprising such modified alleles. Watermelon plants comprising such mutant alleles of the Ts-gene are encompassed herein, as are methods of modifying the endogenous wild type Ts-gene allele (e.g. either by random mutagenesis followed by selection of mutants in the target gene or by targeted mutagenesis of the endogenous Ts gene). The Ts-allele (or a part thereof) may be either deleted from chromosome 2, or its expression may be reduced or knocked out (by e.g., modifying regulatory elements, such as the promoter sequence of the Ts gene), or mutations may be introduced into the allele, whereby the encoded Ts-protein has reduced function or a loss-of-function. Thus, different mutant alleles of the Ts-gene can be made, which either lead to a reduced level of the wild type Ts protein being made or no wild type Ts-protein being made (e.g., expression is knocked down or knocked out), or expression is not affected, but the encoded mutant Ts-protein has reduced activity (reduced function) or no activity (loss of function) compared to the wild type Ts-protein.

The wild type functional Ts-gene was found to encode an Acyl CoA N-acetyltransferase protein (which is also referred to as "Ts-protein" herein or C1NAT protein). In the original tomato seed mutant plant, the entire C1NAT gene was found to be deleted (as part of a ~14 kb deletion on chromosome 2, depicted in SEQ ID NO: 8). This original deletion is found e.g., in seeds of variety WH9716, a representative sample of seeds having deposited under Accession number NCIMB42704, described in U.S. Pat. No. 9,763,399, incorporated herein by reference. As this deletion is large and comprises other genes, new smaller deletions of only the Ts-gene or only a part of the Ts-gene can now be made, or other modifications can be made affecting the Ts-gene expression or function. Furthermore, it was found that certain watermelon plants comprise a mutant allele of the Ts-gene, which results in a reduced function of the encoded C1NAT protein (or Ts protein).

The Ts-gene on chromosome 2, thus, either encodes a) a functional, wild type Ts-protein (haplotype 'WT'), or b) a mutant, reduced function Ts-protein or a reduced level of the wild type Ts-protein (haplotype 'RE'), or c) no functional Ts-protein (haplotype 'NO', e.g., through a deletion of the Ts gene or a part thereof, no expression of the Ts gene or the production of a mutant, non-functional Ts-protein).

As mentioned, these three Ts-gene/Ts-protein possibilities on chromosome 2 (haplotype 'NO', 'RE' or 'WT') interact with two loci on chromosome 6 (one locus comprising either a Guanine, SEQ ID NO: 4, or a Thymine, SEQ ID NO: 5) for the SNP 01 marker and the other comprising either an insertion, SEQ ID NO: 7, or a deletion, SEQ ID NO: 6, for the INDEL 02 marker), resulting in different combinations of alleles (or haplotypes) for the Ts-gene/Ts protein, and for SNP_01 and INDEL_02. These different haplotype combinations determine the final seed size of the watermelon plants, expressed herein as grams/10 seeds (an average of the measurement of three samples of 10 g seeds per line), according to the model of FIG. 2 for inbred lines, such as parent lines. The model can be used to select plants having a certain haplotype for the locus on chromosome 2 and for the two loci on chromosome 6, which plants produce a predicted average seeds size in the fruits they develop. The model can also be used to select parent lines for making F1 hybrids, whereby the haplotype for the locus on chromosome 2 and the two loci on chromosome 6 of the parent lines predicts the average seeds size in the fruits produced by the F1 hybrid plants made from crossing any two selected parent lines. This model is shown in FIG. 3, whereby P1 and P2 represent inbred parent lines with different haplotypes for chromosome 2 (i.e., a Ts-gene with no function (NO), reduced function (RE) or wild type function (WT) of the encoded protein) and with different haplotypes for chromosome 6 (i.e., the haplotype small (S), medium (M) or large (L)).

Table 1 and Table 2 below show the different haplotypes for chromosome 2 and chromosome 6, respectively, and the Ts allele or markers resulting in, or being predictive of the haplotype.

TABLE 1

| Chromosome 2 haplotypes | Possible modifications of the Ts-allele to result in haplotype |
|---|---|
| Haplotype 'NO'—no functional Ts protein being made | Deletion of all or part of the Ts-allele<br>Knock-out of gene expression, by e.g., insertion of DNA into the Ts-allele to prevent e.g., gene expression<br>Knock-out of gene expression, by e.g., modification of one or more regulatory elements, such as the promoter<br>Mutations which result in the encoded protein being non-functional (loss of function Ts protein)<br>For example, NCIMB42704 comprises deletion of Ts-allele as art of a ~14 kb deletion shown in SEQ ID NO: 8 |
| Haplotype 'RE'—Ts protein has reduced function or reduced level of wild type Ts protein being made | One or more amino acids being inserted, deleted or replaced to reduce function of the mutant Ts protein compared to the wild type Ts protein<br>For example, D204Y amino acid substitution in the Ts-protein as found in variety SP-4 (Syngenta)<br>Reduced level of the wild type Ts protein, due to a knock-down of gene expression of the ts-allele, e.g., due to a modification of one or more regulatory elements, such as the promoter |
| Haplotype 'WT'—Ts protein is wild type, functional | No change to Ts-allele<br>Present in most watermelon varieties |

TABLE 2

| Chromosome 6 haplotypes | SNP_01 marker | INDEL_02 marker |
|---|---|---|
| Haplotype 'S' (small) | Comprising nucleotide G for SNP_01, i.e., comprising SEQ ID NO: 4 | Comprising a deletion for INDEL_02, i.e., comprising SEQ ID NO: 6 |
| Haplotype 'M' (medium) | Comprising nucleotide G for SNP_01, i.e., comprising SEQ ID NO: 4 | Comprising an insertion/lacking the deletion for INDEL_02, i.e., comprising SEQ ID NO: 7 |
| Haplotype 'M' (medium) | Comprising nucleotide T for SNP_01, i.e., comprising SEQ ID NO: 5 | Comprising a deletion for INDEL_02, i.e., comprising SEQ ID NO: 6 |
| Haplotype 'L' (large) | Comprising nucleotide T for SNP_01, i.e., comprising SEQ ID NO: 5 | Comprising an insertion/lacking the deletion for INDEL_02, i.e., comprising SEQ ID NO: 7 |

General Definitions

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g., "a plant" refers also to several cells, plants, etc. Similarly, "a fruit" or "a plant" also refers to a plurality of fruits and plants.

A "plant line" or "breeding line" refers to a plant and its progeny. As used herein, the term "inbred line" refers to a plant line which has been repeatedly selfed, as a result of this selfing, plants of an inbred line are nearly identical to each other in genotype and phenotype.

As used herein, the term "mutant allele of a gene" refers to a mutant allele of a gene, said mutant allele either encodes a protein which, compared to the protein encoded by the wild type allele of the gene, comprises one or more amino acids replaced, deleted or inserted, whereby the mutant allele produces a mutant protein which has a "reduced-function" or "loss-of-function" compared to the wild type protein, or said mutant allele of the gene has a reduced gene expression (knock-down) or even no expression (knock-out) compared to the gene expression of the wild type (non-mutated) allele of the gene. Although strictly speaking the term "mutant allele" implies that an allele is present at a locus, the definition herein also encompasses, in one aspect, that the all or part of the allele is absent (deleted) on the chromosome, resulting in no wild type protein being made. For example the entire allele, including promoter and coding sequence, may be deleted, or only part of the allele, e.g., only part of the promoter sequence, may be deleted.

As used herein, the term "plant" includes the whole plant or any parts or derivatives thereof, preferably having the same genetic makeup as the plant from which it is obtained, such as plant organs (e.g., harvested or non-harvested fruits, leaves, etc.), plant cells, plant protoplasts, plant cell- or tissue-cultures from which whole plants can be regenerated, plant calli, plant cell clumps, plant transplants, seeds from which the plant can be grown and seeds produced by the plant, seedlings, plant cells that are intact in plants, plant clones or micropropagations, or parts of plants, such as plant cuttings, embryos, pollen, ovules, fruits (e.g., harvested tissues or organs), flowers, leaves, clonally propagated plants, roots, stems, root tips, grafts (scions and/or root stocks) and the like. Also any developmental stage is included, such as seedlings, cuttings prior or after rooting, etc. As used herein, the term plant includes plant and plant parts comprising one or more of the mutant alleles of the disclosure.

In one aspect, the term plant part refers to plant cells, or plant tissues or plant organs that comprise one or more of the mutant alleles of the disclosure. In one aspect, a plant part can grow into a plant and/or live on photosynthesis (i.e., synthesizing carbohydrate and protein from the inorganic substance, such as water, carbon dioxide and mineral salt). In another aspect, a plant part cannot grow into a plant and/or live on photosynthesis (i.e., synthesizing carbohydrate and protein from the inorganic substance, such as water, carbon dioxide and mineral salt). Thus, a plant part can be propagating or non-propagating.

As used herein, the term "variety" or "cultivar" or "plant variety" means a plant grouping within a single botanical taxon of the lowest known rank, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one locus or gene or two loci or genes, but which can otherwise differ from one another enormously as regards the other loci or genes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). These may be identical alleles of the gene (homozygous) or two different alleles (heterozygous), e.g. two identical copies of the mutant ts-allele (i.e. ts/ts) or one copy of the mutant ts-allele and one copy of the wild type allele (i.e. ts/Ts). Likewise a triploid plant is referred to as homozygous for the gene if it has three identical alleles of a gene (e.g. three copies of the mutant ts-allele, i.e. ts/ts/ts) and a tetraploid plant is referred to as homozygous for the gene if it has four identical alleles of the gene, e.g. four copies of the mutant ts-allele (i.e. ts/ts/ts/ts).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Vegetative propagation" refers to propagation of plants from vegetative tissue, e.g., by in vitro propagation or grafting methods (using scions).

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of e.g., at least 3, 4, 5, 6, 7, 8 or more plants (or plant parts) are measured (depending on the trait), preferably in randomized experimental designs with several replicates and suitable control plants grown under the same conditions in the same experiment. For measuring average seed size in fruits herein, to e.g., make a selection of lines according to the seed-size models here, it is sufficient to weigh 3 samples of 10 seeds of a seedlot of a line, whereby the seedlot is composed of all seeds harvested from at least three fruits of at least three plants of a genotype.

"Statistically significant" or "statistically significantly" different or "significantly" different refers to a characteristic of a plant line or variety that, when compared to a suitable control (e.g., the genetic control) show a statistically significant difference in that characteristic (e.g., the p-value is less than 0.05, $p<0.05$, using ANOVA) from the mean of the control.

The term "nucleic acid sequence" (or nucleic acid molecule) refers to a DNA or RNA molecule in single or double stranded form, particularly a DNA encoding a protein or protein fragment according to the disclosure. An "isolated nucleic acid sequence" refers to a nucleic acid sequence which is no longer in the natural environment from which it was isolated, e.g., the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g., an mRNA or an RNAi molecule) in a cell, operably linked to suitable regulatory regions (e.g., a promoter). A gene may thus comprise several operably linked sequences, such as a promoter, a 5' leader sequence comprising e.g., sequences involved in translation initiation, a (protein) coding region (cDNA or genomic DNA) and a 3' non-translated sequence comprising e.g., transcription termination sites. A gene may be an endogenous gene (in the species of origin) or a chimeric gene (e.g., a transgene or cis-gene).

"Expression of a gene" refers to the process wherein a DNA region, which is operably linked to appropriate regulatory regions, particularly a promoter, is transcribed into an RNA.

An "active protein" or "functional protein" is a protein which has protein activity as measurable in vivo, e.g., by the phenotype conferred by the protein. A "wild type" protein is a fully functional protein, as present in the wild type plant. A "mutant protein" is herein a protein comprising one or more mutations in the nucleic acid sequence encoding the protein, whereby the mutation(s) results in (the mutant allele encoding) a "reduced-function" or "loss-of-function" protein, as e.g., measurable in vivo, e.g., by the phenotype conferred by the mutant allele (in homozygous form). A mutant protein may thus have one or more amino acids inserted, deleted or replaced compared to the wild type protein, whereby the normal wild type function of the protein is reduced or abolished.

"Ts gene" or "Tomato-seed gene" is a single gene identified in cultivated watermelon on chromosome 2, which when mutated affects average seed size. 'Ts' is the wild type (WT), functional allele as present in cultivated watermelon plants in homozygous form having large seeds and 'ts' is the mutant allele resulting in smaller seed size than the wild type allele, depending on the functionality of the allele and encoded protein. In one aspect the Ts gene is the gene encoding a protein of SEQ ID NO: 1 or encoding a protein comprising at least 90%, 91%, 92%, 93%, 94%, 95%, 96%, 97% or 98% sequence identity to SEQ ID NO: 1, when aligned pairwise using e.g. Emboss-Needle with default parameters.

A "reduced function Ts-protein" or "reduced activity Ts-protein" refers to a mutant protein which has a reduced activity and confers a significant reduction in average seed size in the fruits of a plant comprising such reduced function protein at least when the allele encoding the mutant protein is present in homozygous form compared to a control plant comprising the wild type Ts-allele in homozygous form. Likewise a loss-of-function Ts-protein refers to a protein which has no activity and confers a significant reduction in average seed size in the fruits of a plant comprising such loss-of-function protein at least when the allele encoding the mutant protein is present in homozygous form compared to a control plant comprising the wild type allele in homozygous form. The phenotype of the mutant ts-allele and the wild type Ts-allele should be compared in the same genetic background regarding the haplotype on chromosome 6, i.e., having a chromosome 6 haplotype 'S' (small), 'M' (Medium) or 'L' (Large).

"Haplotype" or "haploid genotype" refers to the genotype of one or several genetic loci in a plant. The chromosome 2 haplotype is herein determined by the locus on chromosome 2, where the Ts-gene is found. Three chromosome 2 haplotypes can be distinguished (see also Table 1): no functional Ts-protein being present (indicated as haplotype 'NO'), due to e.g., either a deletion of all or part of the Ts-gene, or a mutant allele of the gene being present having no expression or a mutant allele of the gene being present encoding a loss-of-function Ts protein), a reduced function Ts-protein being present (indicated as 'RE') due to a mutant ts-allele being present encoding a reduced function Ts-protein or reduced level of the wild type Ts-protein being made, or a wild type, function Ts-protein being present (indicated as 'WT). The chromosome 6 haplotype is herein determined by two loci on chromosome 6, the SNP_01 marker genotype and the INDEL_02 marker genotype, see also Table 2. The chromosome 6 haplotype of a plant may be 'S' (small), 'M' (Medium) or 'L' (Large). The haplotype 'S' means that the chromosome 6 of the plant comprises SEQ ID NO: 4 and SEQ ID NO: 6. The haplotype 'M' means that the chromosome 6 of the plant comprises SEQ ID NO: 4 and SEQ ID NO: 7 or SEQ ID NO: 5 and SEQ ID NO: 6. The haplotype 'L' means that the chromosome 6 of the plant comprises SEQ ID NO: 5 and SEQ ID NO: 7. The plant preferably comprises two copies of the same haplotype (is homozygous). See also FIG. 2.

"Induced mutant alleles" are mutant alleles in which the mutation(s) is/are/have been induced by human intervention, e.g., by mutagenesis via physical or chemical mutagenesis methods, or via e.g., tissue culture (as described in e.g., Zhang et al, Plos 9(5) e96879), including also genome editing techniques, such as Crispr based techniques.

A "mutation" in a nucleic acid molecule coding for a protein is a change of one or more nucleotides compared to the wild type sequence, e.g., by replacement, deletion or insertion of one or more nucleotides. Examples of such a mutation are point mutation, nonsense mutation, missense mutation, splice-site mutation, frame shift mutation or a mutation in a regulatory sequence.

A "point mutation" is the replacement of a single nucleotide, or the insertion or deletion of a single nucleotide.

A "nonsense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "missense" or non-synonymous mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation in a nucleic acid sequence encoding a protein by which the reading frame of the mRNA is changed, resulting in a different amino acid sequence. The resulting protein may have reduced function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid, but preferably at least 10, 20, 30, 40, 50, 60, 70, 80, 90, 100 or more amino acids, at either the N-terminus or the C-terminus of the protein is missing compared to the amino acid sequence of the corresponding wild type protein. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence. "Amino acid substitution" or "amino acid replacement" refers to one or more amino acids of the wild type protein being replaced by different amino acids. A "disfavourable" amino acid replacement means that the properties of the replaced amino acid are substantially different from the original amino acid (e.g. in charge, size, polarity, hydrophobicity, structure, etc.) and may thus negatively affect protein properties, such as 3-dimensional folding, interaction with other amino acids or compounds, etc. and may thus reduce or even abolish the in vivo activity of the protein. Disfavourable amino acid replacements can be found on the world wide web at russelllabs.org/aas/aas.html. Here also all properties of the different amino acids are found.

A mutation in a regulatory sequence, e.g., in a promoter of a gene, is a change of one or more nucleotides compared to the wild type sequence, e.g., by replacement, deletion or insertion of one or more nucleotides, leading for example to reduced or no mRNA transcript of the gene being made. In one aspect, a mutation in a regulatory sequence of a protein includes a lower level of wild type protein (e.g., due to a lower expression of the allele) or no wild type protein being made (no expression of the allele). Mutations in regulatory elements, such as promoters, can be generated by e.g., CRISPR/Cas. Rodriguez-Leal et al., 2017, Cell 171, 470-480 describe for example mutating cis-regulatory elements to create a continuum of mutant alleles with different expression.

A "mutation" in a protein is a change of one or more amino acid residues compared to the wild type sequence, e.g., by replacement, deletion, truncation or insertion of one or more amino acid residues.

"Mutant protein" is herein a protein comprising one or more mutations in the nucleic acid sequence encoding the protein, whereby the mutation results in (the mutant nucleic acid molecule encoding) a reduced-function or loss-of-function protein, as e.g. measurable in vivo, e.g. by the phenotype conferred by the mutant allele.

"Knock-out" or "entire knock-out" shall be understood that expression of the respective gene is not detectable anymore.

"Loss-of-function" or "reduced-function" or "decreased function" shall mean in context of the present invention that the protein, although possibly present in amounts equal or similar to a corresponding wild type protein, does not evoke its normal effect anymore, e.g. for mutant alleles encoding such a protein when present in homozygous form in a diploid plant, the phenotype affected by the gene will be changed compared to the plant homozygous for the wild type allele.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g., a dsRNA or hairpin RNA capable of silencing the endogenous target gene expression). In mutagenesis or targeted gene editing approaches, a target gene is the endogenous gene which is to be mutated (and/or in which mutations are selected by e.g., TILLING) or edited, leading to a change in (reduction or loss of) gene expression or a change in (reduction or loss of) function of the encoded protein.

"Targeted gene editing" is referred to techniques whereby endogenous target genes can be modified, e.g. one or more nucleotides can be inserted, replaced and/or deleted e.g. in the promoter or coding sequence. For example CRISPR based techniques, such as Crispr-Cas9 gene editing, Crispr-Cpf1 gene editing, or more recent techniques called 'base editing' or 'primer editing' can be used to modify endogenous target genes, such as the endogenous wild type Ts gene in watermelon. As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

As seed length and seed width correlate with each other, the seed size may be measured as the weight of 10 seeds (gram/10 seeds). The term "seed size" (SSZ) or "average seed size" refers to the average seed weight of at least three measurements of 10 seeds of a seedlot of a genotype. A seedlot of a genotype (e.g., a line or an F1 hybrid) is made by harvesting at least three fruits of at least three plants of the genotype.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g., 100 nt) are for example those which include at least one wash in 0.2×SSC at 63° C. for 20 min, or equivalent conditions. Stringent conditions for DNA-DNA hybridization (Southern blots using a probe of e.g., 100 nt) are for example those which include at least one wash (usually 2) in 0.2×SSC at a temperature of at least 50° C., usually about 55° C., for 20 min, or equivalent conditions.

"Sequence identity" and "sequence similarity" can be determined by alignment of two peptide or two nucleotide sequences using global or local alignment algorithms. Sequences may then be referred to as "substantially identical" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimizes the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, accessible at world wide web under ebi.ac.uk/Tools/emboss/. Alternatively sequence identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 90%, 91%, 93%, 94%, 95%, 96%, 97%, 98% or 99% or more (as determined by Emboss "needle" using default parameters, i.e., gap creation penalty=10, gap extension penalty=0.5, using scoring matrix DNAFULL for nucleic acids an Blosum62 for proteins). Such sequences are also referred to as 'variants' herein, e.g., other allelic variants of the Ts-alleles and Ts-proteins than the specific nucleic acid and protein sequences disclosed herein can be identified.

"Wild type Ts-allele" (WT) or "Ts allele" refers herein to a version of a gene encoding a fully functional watermelon Ts-protein (wild type Ts-protein). A sequence encoding a fully functional Ts-protein of SEQ ID NO: 1 is for example the wild type Ts cDNA (mRNA) sequence depicted in SEQ ID NO: 3, or the wild type Ts-genomic sequence depicted in SEQ ID NO: 2. The protein sequence encoded by this wild type Ts-mRNA is depicted in SEQ ID NO: 1. It consists of 412 amino acids. Other fully functional Ts-protein-encoding alleles (i.e., variant alleles, or allelic variants) may exist in other watermelon plants and may comprise substantial sequence identity with SEQ ID NO: 1 (when aligned pairwise using e.g. Emboss-Needle), i.e., at least about 90%, 91%, 93%, 94%, 95%, 96%, 97%, 98% or 99% sequence identity with SEQ ID NO: 1. Such fully functional wild type Ts-proteins are herein referred to as "variants" or "functional variants" of SEQ ID NO: 1.

"Mutant ts allele" or "ts allele" refers herein to a mutant allele of the Ts gene on chromosome 2 in watermelon, which causes the fruits of the plant to produce smaller seeds (than in a plant homozygous for the wild type Ts allele) at least when the mutant allele is in homozygous form. The mutation in the mutant allele can be any mutation or combination of mutations, including deletions, truncations, insertions, point mutations, non-sense mutations, mis-sense mutations or non-synonymous mutations, splice-site mutations, frame shift mutations and/or mutations in one or more regulatory sequences such as promoter sequence, or enhancer or silencer sequences. In one aspect the mutant ts allele is a mutant allele of the Ts gene whereby the Ts gene is the gene encoding a protein of SEQ ID NO: 1 or encoding a protein comprising at least 90%, 91%, 92%, 93%, 94%, 95%, 96%, 97% or 98% or 99% sequence identity to SEQ ID NO: 1 (when aligned pairwise).

"Acetyl transferase domain" is a conserved protein domain which is involved in catalysis of the transfer of an acetyl group to a nitrogen atom on the acceptor molecule. The Ts-proteins of SEQ ID NO: 1 has such a domain starting at amino acid 54 and ending at amino acid 146. The domain can be identified by having high sequence identity with the Pfam domain PF00583, e.g., by doing a sequence analysis on the world wide web at pfam.xfam.org or by analyzing the sequence in InterPro, on the www site ebi.ac.uk/interpro/search/sequence-search.

"Provean analysis" (Protein Variation Effect Analyzer) is a software tool which predicts whether an amino acid substitution or indel has an impact on the biological function of a protein. This tool can be used on the world wide web at provean.jcvi.org/index.php. Provean analysis for example predicts that the D204Y substitution in SEQ ID NO: 1 reduces Ts-protein function, by indicating that the substitution is 'deleterious' in the analysis. The same analysis can be done for other amino acid changes in the Ts-protein. As this analysis is merely a prediction, the real effect on Ts-protein function needs to be confirmed by generating a plant comprising the mutant allele and confirming the phenotypic change.

"Watermelon plant" or "cultivated watermelon" or "domesticated watermelon" or "*Citrullus lanatus*" refers to plants of *Citrullus lanatus* ssp. vulgaris, i.e., varieties, breeding lines or cultivars, cultivated by humans and having good agronomic characteristics, especially producing edible and marketable fruits of good size and quality and uniformity; such plants are not "wild watermelon" or "primitive watermelon" plants, i.e., plants which generally have much poorer yields and poorer agronomic characteristics than cultivated plants and are less uniform genetically and in their physiological and/or morphological characteristics. "Wild plants" or "wild watermelon" include for example ecotypes, landraces or wild accessions or wild relatives of a species, such as for example accessions of *Citrullus lanatus* ssp. *lanatus, Citrullus lanatus* ssp. mucosospermus, *Citrullus colocynthis*, or plants of the *citroides* group (e.g., *C. lanatus* var. *citroides*) producing e.g., fruits of poor quality and/or poor uniformity.

"Landrace(s)" refers to primitive cultivars developed in local geographic regions, which often show a high degree of genetic variation in their genome and exhibit a high degree of morphological and/or physiological variation within the landrace (e.g., large variation in fruit size, etc.), i.e., are significantly less uniform than cultivated plants. Landraces are, therefore, herein included in the group "wild" plants, which is distinct from "cultivated" plants.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g., at least 4, 5, 6, 7 or more) of inbreeding, resulting in a plant line with a high uniformity.

"Uniformity" or "uniform" relates to the genetic and phenotypic characteristics of a plant line or variety. Inbred lines are genetically highly uniform as they are produced by several generations of inbreeding. Likewise the F1 hybrids which are produced from crossing two such inbred lines are highly uniform in their genotypic and phenotypic characteristics and performance.

A "recombinant chromosome" refers to a chromosome having a new genetic makeup arising through crossing-over between homologous chromosomes. For example, a recombinant chromosome may comprise an introgression fragment from a wild plant, which introgression fragment comprises e.g., a mutant allele.

The term "traditional breeding techniques" encompasses herein crossing, backcrossing, selfing, selection, double haploid production, embryo rescue, protoplast fusion, marker assisted selection, mutation breeding etc., all as known to the breeder (i.e., methods other than genetic modification/transformation/transgenic methods), by which, for example, a recombinant chromosome or a mutant allele can be obtained, identified and/or transferred.

A genetic element, an introgression fragment, or a gene or allele conferring a trait (such as seed size) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Cultivated watermelons containing the genetic element, locus, introgression fragment, gene or allele (e.g. a mutant is allele) can be generated de novo, e.g. by mutagenesis (e.g. chemical mutagenesis, CRISPR-Cas induced, etc.) and then e.g. be crossed into other cultivated watermelons.

"Backcrossing" refers to a breeding method by which a (single) trait, such as a mutant allele, can be transferred from a generally (but not necessarily) inferior genetic background (e.g., a wild plant or wild relative; also referred to as "donor") into a generally (but not necessarily) superior genetic background (also referred to as "recurrent parent"), e.g., a cultivated plant. An offspring of a cross (e.g., an F1 plant obtained by crossing a donor plant with a e.g., superior genetic background plant; or an F2 plant or F3 plant, etc., obtained from selfing the F1) is e.g., "backcrossed" to the recurrent parent genetic background, e.g., to the cultivated parent. After repeated backcrossing, the trait of the donor genetic background will have been incorporated into the recurrent parent genetic background.

"Vegetative propagation", "vegetative reproduction" or "clonal propagation" are used interchangeably herein and mean the method of taking part of a plant and allowing that plant part to form at least roots where plant part is, e.g., defined as or derived from (e.g., by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation. In one aspect, propagation by grafting, e.g., a scion onto a rootstock, is included herein.

"Cell culture" or "tissue culture" refers to the in vitro culture of cells or tissues of a plant.

"Regeneration" refers to the development of a plant from cell culture or tissue culture or vegetative propagation.

"Non-regenerable cell" refers to a cell which cannot be regenerated into a whole plant.

"M1 generation" or "M1 plants" in context with the present invention shall refer to the first generation that is produced directly from the mutagenic treatment. A plant grown from seeds treated with a mutagen e.g., is a representative of an M1 generation.

"M2 generation" or "M2 plant" shall refer herein to the generation obtained from self-pollination of the M1 generation. A plant grown from seeds obtained from a self-pollinated M1 plant represents a M2 plant.

FIGURES

FIG. 1 depicts wild type Ts protein of watermelon cv 97301 (SEQ ID NO: 1); D204 is highlighted in bold, as the mutant D204Y is one of the is-gene mutant alleles which results in a reduced function of the encoded C1NAT protein (also referred to as Ts protein herein). The conserved Acetyl transferase domain is underlined.

FIG. 2 shows predicted seed size model for selecting inbred watermelon lines comprising different alleles for seed size, based on the interaction between the Ts-gene on chromosome 2 (producing either no functional Ts-protein, indicated as NO, or a reduced function Ts-protein or a reduced level of wild type Ts-protein, indicated as RE, or a wild type functional Ts-protein, indicated as WT) and two loci on chromosome 6, referred to as SNP_01 and INDEL_02 markers or loci. The combination of the SNP_01 and the INDEL_02 genotype is referred to as the chromosome 6 seed size "haplotype", which may be a 'small' (S) seed size haplotype, a 'medium' (M) seed size haplotype or a 'large' (L) seed size haplotype. For example, a diploid watermelon plant which is homozygous for a is-gene on chromosome 2 which results in no functional Ts protein being made (chromosome 2 haplotype is 'NO'), and which is further homozygous for Guanine of SNP_01 (i.e., homozygous for SEQ ID NO: 4) and is homozygous for the deletion of INDEL_02 (i.e., homozygous for SEQ ID NO: 6), i.e., which has a 'small' (S) haplotype for chromosome 6, is predicted to have very small seeds in the fruits, having an average seed weight of about 0.07 g per 10 seeds. The correlation between the predicted and the actual seed sizes measured for each genotype is 89% ($R^2$=0.89) as can be seen in FIG. 4. The actual seed size of an individual line may thus deviate from the predicted seed size, but given the high correlation the model is very useful in generating and/or selecting inbred lines having a certain predicted average seed size in their fruits.

FIG. 3 shows predicted Seed Size Model for selecting parent lines for F1 hybrid seed production. P1 and P2 are parent lines, having either a Ts-gene on chromosome 2, which results in either no functional Ts-protein (indicated as NO), a reduced function Ts-protein or a reduced level of wild type Ts-protein (indicated as RE) or a wild type functional Ts-protein (indicated as WT), and having further a certain haplotype for the chromosome 6 SNP_01 and INDEL_02 markers or loci, e.g., either a 'small' (S), 'medium' (M) or 'large' (L) haplotype for chromosome 6, as shown in FIG. 2 in detail. The F1 hybrid seed made by crossing P1 and P2, or the F1 hybrid plants grown therefrom, are predicted to comprise a certain predicted seed size (indicated in g/10 seeds) in the fruits of the F1 hybrid plants. The correlation between predicted and actual seed size measured for hybrids is 82% ($R^2=0.82$) as seen in FIG. 5, and thus the actual seed size of an individual F1 hybrid genotype may deviate from the predicted seed size, but given the high correlation the model is very useful in crossing generated and/or selected inbred parent lines to generate F1 hybrids having a certain predicted seed size in their fruits.

Figure 6:
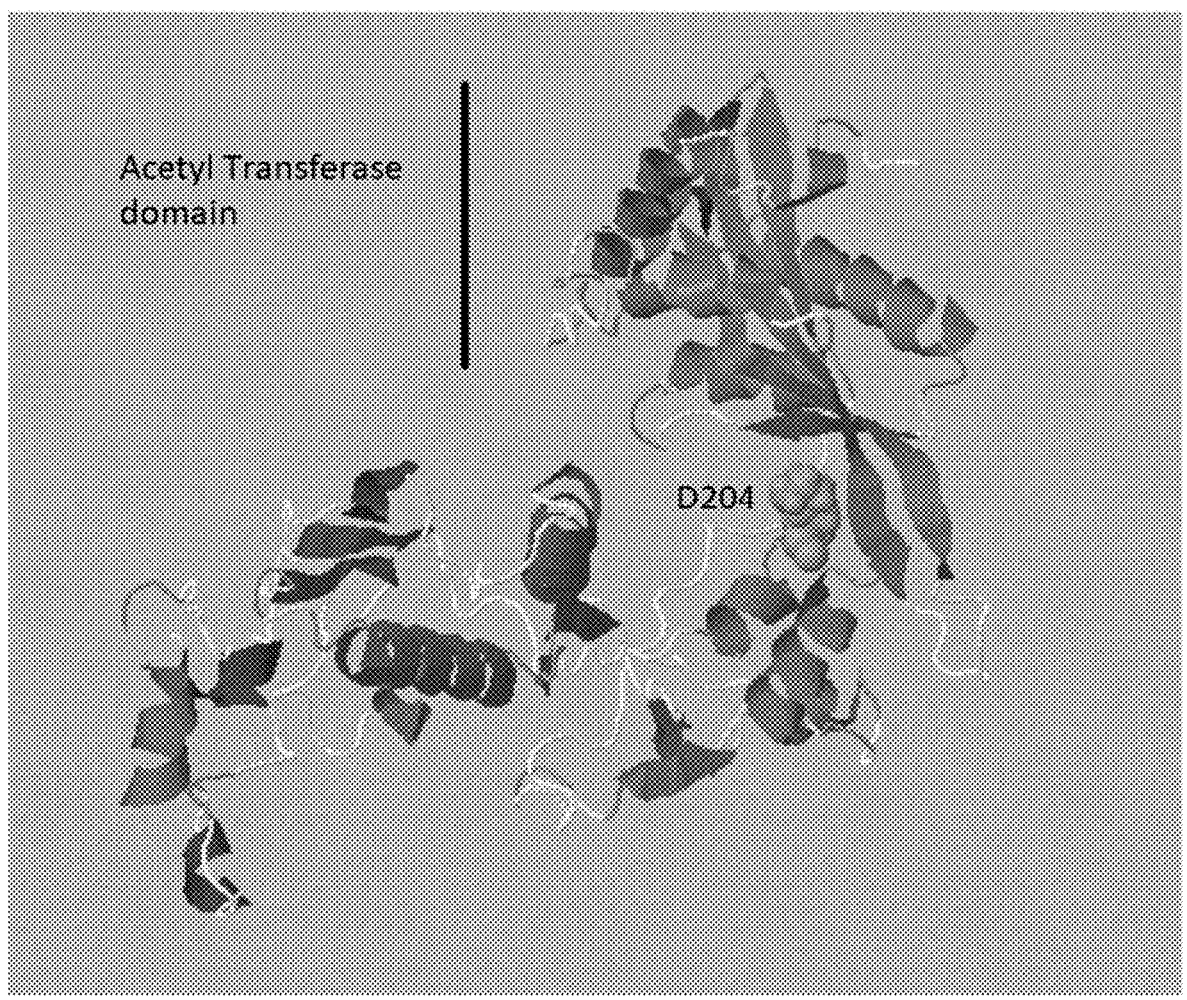

FIG. 6 shows a 3-dimensional structure of the wild type, functional Ts-protein, with D204 (which is present in the middle domain of the protein) highlighted. The N-terminal domain contains the conserved Acetyl transferase domain. The structure was generated by RaptorX structure prediction (world wide web at //raptorx.uchicago.edu/).

Figure 7:
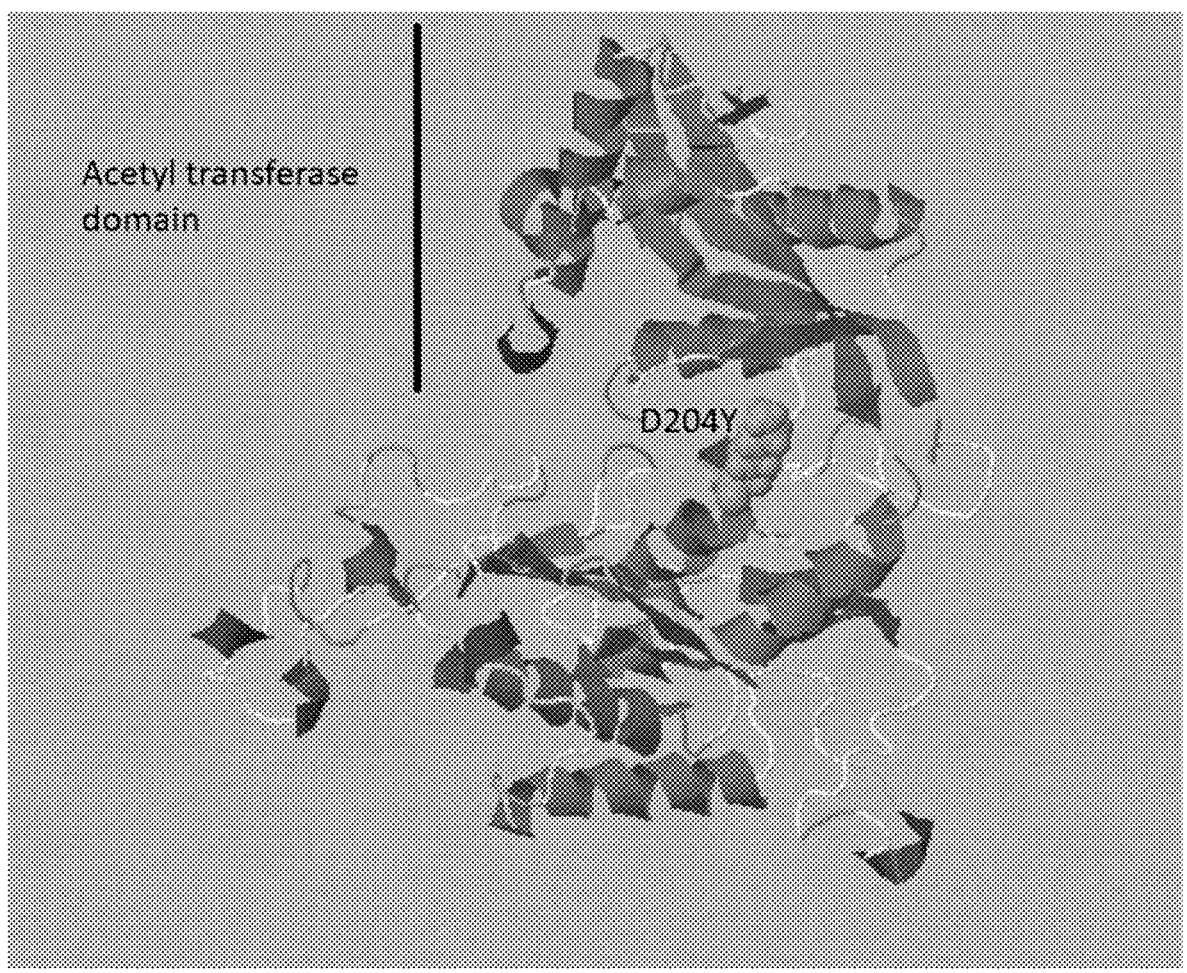

FIG. 7 shows a 3-dimensional structure of the D204Y mutant Ts-protein, with 204Y (which is present in the middle domain of the protein) highlighted. The N-terminal domain contains the conserved Acetyl transferase domain. The structure was generated by RaptorX structure prediction (world wide web at //raptorx.uchicago.edu/).

Description of Sequences
  SEQ ID NO: 1—wild type Ts-protein of watermelon (genome 97103 v1 and v2)
  SEQ ID NO: 2—genomic DNA encoding the wild type Ts-protein of SEQ ID NO: 1
  SEQ ID NO: 3—cDNA encoding the wild type Ts-protein of SEQ ID NO: 1
  SEQ ID NO: 4—chromosome 6 SNP 01 marker comprising a Guanine (G) at nucleotide 61
  SEQ ID NO: 5—chromosome 6 SNP 01 marker comprising a Thymine (T) at nucleotide 61
  SEQ ID NO: 6—chromosome 6 INDEL marker comprising a deletion of 46 nucleotides
  SEQ ID NO: 7—chromosome 6 INDEL marker not comprising a deletion/i.e., comprising an insertion of 46 nucleotides compared to SEQ ID NO: 6
  SEQ ID NO: 8—large, genomic deletion on chromosome 2 found to comprise the genomic DNA of SEQ ID NO: 2; SEQ ID NO: 8 is deleted/absent in chromosome 2 of variety WH9716, a representative sample of seeds having deposited under Accession number NCIMB42704.

A representative sample of seeds of NCIMB42704 have been deposited at the NCIMB Ltd. (Ferguson Building, Craibstone Estate, Bucksburn, Aberdeen AB21 9YA, Scotland, UK) under the Budapest Treaty by Nunhems B. V. on 12 Dec. 2016 and may be used as described herein.

Mutations in the Ts-Gene of Watermelon

As the Ts-gene has been identified on chromosome 2, mutant alleles of the Ts-gene can be generated de novo in watermelon. This can be done by e.g., non-targeted mutagenesis techniques (chemical or radiation induced mutations) or targeted mutagenesis techniques or gene editing techniques, such as Crispr based techniques (Crispr—Cas9, Crispr—CpfI, etc.).

The Ts-gene has been identified in watermelon and it encodes the wild type Ts-protein of SEQ ID NO: 1. However, allelic variants of the Ts-gene may be present in other watermelon lines or varieties or in wild relatives of watermelon, e.g., alleles encoding functional Ts-proteins comprising at least 90%, 91%, 92%, 93%, 94%, 95%, 96%, 97%, 98% or more amino acid sequence identity to SEQ ID NO: 1. Mutant alleles of such allelic variants of the Ts-gene can be generated and/or identified, which result in a reduced seed size in watermelon plants homozygous for the mutant allele, compared to a plant homozygous for the wild type allele.

Mutant alleles can affect the expression of the Ts-gene, e.g., knock-down expression of the endogenous Ts-gene or knock-out expression of the gene, leading to a reduced amount of the functional, wild type Ts-protein being present in the plant in tissues and under conditions when the Ts-gene is expressed, or even no wild type Ts-protein being present in the plant, at least when such a mutant allele is in homozygous form. Such mutant alleles can be generated by mutations in the regulatory elements of the Ts-gene, in particular the promoter of the Ts-gene.

The decrease in the expression of an Ts-gene or ts-allele can, for example, be determined by measuring the quantity of RNA transcripts encoding Ts proteins (e.g., mRNA), e.g., using Northern blot analysis or RT-PCR. Here, a reduction preferably means a reduction in the amount of transcripts by at least 10%, 20%, 30%, 40%, 50%, in particular by at least 60% or 70%, preferably by at least 80% or 85% or by at least 90% or 95% or 100%, compared to the wild type allele. If the decrease is 100% this is a knock-out of the ts-allele, otherwise it is referred to as a knock-down.

The decrease in the amount of Ts protein, which results in a reduced activity of these proteins in the plant cells or plants concerned, can, for example, be determined by immunological methods such as Western blot analysis, ELISA (Enzyme Linked Immuno Sorbent Assay) or RIA (Radio Immune Assay). Here, a decrease preferably means a reduction in the amount of Ts proteins by at least 10%, 20%, 30%, 40%, 50%, in particular by at least 60% or 70%, or by at least 80%, 85%, 90% or by at least 95% or 100% compared to the protein made by the wild type allele.

Alternatively, mutant alleles can affect the activity of the Ts-protein encoded by the is-gene, e.g., the mutant allele may be expressed normally (ts-gene expression level being the same as the wild type allele), but the protein made may comprise one or more amino acids inserted, deleted and/or replaced compared to the wild type, functional Ts-protein. Such a mutant Ts-protein may therefore have reduced function or even no activity at all (loss-of-function) in the plant compared to the wild type protein of SEQ ID NO: 1, or compared to a functional variant comprising at least 90% amino acid identity to SEQ ID NO: 1. The mutation(s) may for example change the 3-dimensional structure of the protein, or change its ability to bind certain ligands and carry out its normal function. Provean analysis can, for example, predict whether an amino acid change has an effect on the function of the protein. Of course, whether the prediction is correct should to be tested in vivo, by e.g., comparing the phenotype between a line homozygous for the mutant allele to the phenotype of a line homozygous for the wild type allele. Also 3-dimensional structure predictions can be made, using e.g. RaptorX. FIGS. 6 and 7 show the predicted protein structure of the wild type Ts-protein (FIG. 6) and a mutant Ts-protein, wherein D204 is replaced by Y (FIG. 7). The mutant protein has a reduced function in vivo, as known from the phenotype when the allele is in homozygous form. The reduced function is therefore due to the replacement of amino acid D204 by Y, which is a disfavourable amino acid replacement. D is a negatively charged, polar amino acid, while Y is an aromatic, partially hydrophobic amino acid. The predicted 3-dimensional structures seem somewhat different for the wild type and the mutant protein, which may cause the reduced function.

In one aspect herein, a reduced function Ts-protein is therefore a protein in which one or more amino acids are replaced by one or more other amino acids, especially by one or more disfavourable amino acids. In one aspect the predicted 3-dimension structure of the mutant protein deviates from the predicted structure of the wild type protein.

As the present inventors have found a difference in phenotype regarding average seed size in inbred watermelon plants, dependent on the presence of either a) a functional, wild type Ts-protein (large seed size), or b) a reduced function Ts-protein (medium seed size) or c) no functional Ts-protein (small seed size), as shown in FIG. 2 (right column), the skilled person can easily test whether or not a certain mutant allele encodes a functional, reduced function or non-functional Ts-protein by determining the phenotype when the mutant allele is in homozygous form. The mutant allele should be compared to the wild type allele in the same genetic background regarding the haplotype on chromosome 6. Thus, e.g., the original, non-mutated plant line may be used as control line.

Various technologies exist which can be used to introduce mutations into a Ts-allele, such as targeted mutagenesis or random mutagenesis (using e.g., chemical mutagens, radiation, etc.). For example a population of mutagenized watermelon plants, such as an M2 population, can be screened for mutations in the endogenous Ts-gene being present. This can for example be done using TILLING (Targeting Induced Local Lesions IN Genomes), which has been described by McCallum et al. (2000, Plant Physiology 123, 439-442). Such a method of identifying mutants in the Ts-allele are encompassed herein, as are plants and plant parts comprising such mutant ts-alleles.

When a plant comprising a mutant ts-allele, such as an allele encoding a protein comprising one or more amino acids being inserted, deleted or replaced compared to the wild type Ts protein encoded by the wild type Ts-allele, has been identified, the plants can be selfed to generate a plant homozygous for the mutant allele and such plants can then be grown and phenotyped for average seed size of the seeds produced in the fruits of the plants (after self-pollination). Thus, mature fruits can be harvested and the seeds can be weighed. The average seed weight of e.g., at least three measurements of 10 seeds of a seedlot can then be compared to the average seed weight of the control plant in which the wild type Ts-allele is present (e.g., the non-mutated starting line). Preferably, several plants (e.g., at least 3, 4, 5 or more) comprising the mutant allele and several control plants are grown under the same environment in order to compare the phenotypes (average seed size in the fruits). Preferably the average seed size is determined by taking three (or more) weight measurements of 10 seeds of a seedlot. A seedlot is preferably composed of the seeds of several fruits (e.g., three or more) of several plants (e.g., three or more) of a line. If the average seed size of the plant comprising the mutant allele is significantly reduced compared to the average seed size of the control, then a mutant allele has been identified which can be used for watermelon breeding.

Thus, in one aspect, the mutant allele encodes a mutant Ts-protein which comprises one or more amino acids inserted, deleted or replaced compared to the functional wild type Ts-protein. In principle, any amino acid insertion, deletion and/or replacement compared to the functional wild type protein may lead to the mutant protein having reduced function or no function, i.e., resulting in a reduction in seeds size when the mutant allele is in homozygous form.

One embodiment of the disclosure, therefore, concerns watermelon plant cells, plant parts or plants comprising a mutant allele of a Ts-protein-encoding gene characterized in that the mutant allele comprises or effects one or more of the mutations of:

a) a deletion, truncation, insertion, point mutation, nonsense mutation, missense or non-synonymous mutation, splice-site mutation, frame shift mutation in the genomic sequence;
b) a mutation in one or more regulatory sequences;
c) a deletion, truncation, insertion, point mutation, nonsense mutation, missense or non-synonymous mutation, splice-site mutation, frame shift mutation in the coding sequence;
d) a deletion, truncation, insertion, point mutation, nonsense mutation, missense or non-synonymous mutation, splice-site mutation, frame shift mutation in the pre-mRNA or mRNA; and/or
e) a deletion, truncation, insertion or replacement of one or more amino acids in the Ts-protein.

In one aspect, the mutant allele results in reduced expression or no expression of the is-gene or the mutant allele encodes a mutant Ts-protein having a decreased function or a loss-of-function.

Therefore, in one aspect, a watermelon plant or plant part is provided comprising at least one copy of a mutant allele of a gene name Ts-gene, wherein said mutant allele results in reduced expression or no expression of the Ts-gene, said gene encoding a wild type, functional Ts-protein of SEQ ID NO: 1 or a functional protein comprising at least 90%, 91%, 92%, 93%, 94%, 95%, 96%, 97%, 98% or 99% sequence identity to SEQ ID NO: 1, or wherein said mutant allele encodes a mutant Ts-protein having a decreased function or a loss-of-function compared to the wild type Ts-protein.

A watermelon plant or plant part is provided comprising at least one copy of a mutant allele of a gene named Ts-gene, said Ts-gene encodes a functional Ts-protein of SEQ ID NO: 1 or a protein comprising at least 90%, 91%, 92%, 93%, 94%, 95%, 96%, 97%, 98% or 99% sequence identity to SEQ ID NO: 1, wherein the mutant allele has reduced expression or no expression compared to the wild type allele of the Ts-gene, or wherein the mutant allele encodes a mutant Ts-protein having reduced functioned or loss of function compared to the wild type Ts-protein of SEQ ID NO: 1 or the wild type Ts-protein comprising at least 90%, 91%, 92%, 93%, 94%, 95%, 96%, 97%, 98% or 99% sequence identity to SEQ ID NO: 1.

Thus, a watermelon plant or plant part is encompassed herein comprising at least one copy of a mutant allele of a gene named Ts-gene, said Ts-gene encodes a Ts-protein of SEQ ID NO: 1 or a (functional) protein comprising at least 90%, 91%, 92%, 93%, 94%, 95%, 96%, 97%, 98% or 99% sequence identity to SEQ ID NO: 1 (i.e., a functional variant of the protein of SEQ ID NO: 1), wherein the mutant allele has reduced expression or no expression compared to the wild type allele of the Ts-gene, or wherein the mutant allele encodes a mutant Ts-protein having reduced functioned or loss of function compared to the wild type Ts-protein.

Functional variants of the Ts-protein may exist in different watermelon lines or varieties or even wild watermelon plants or wild relatives of watermelon. Such functional variants can be identified by e.g., sequencing or RT-PCR to analyze the mRNA transcripts and aligning the amino acid sequence with SEQ ID NO: 1 or the genomic sequences with SEQ ID NO: 2. Such an alignment is preferably done using pairwise alignment methods, such as the program Emboss Needle (using the default parameters). The phenotype of the allele can be analyzed in a line homozygous for the variant Ts-allele and from the phenotype one can also conclude whether or not the Ts-allele encodes a functional Ts-protein, by looking at the average seed size of the fruits produced by the plant. If such a variant allele is present in wild material, it may first need to be crossed into a cultivated watermelon line before determining the phenotype and functionality. Mutant alleles of such functional variants can be made in the same way as described herein for making mutant alleles for SEQ ID NO: 1 (e.g. by mutagenesis techniques or gene editing techniques).

The mutant allele reduces the average seed size in the fruits of said plant when the mutant allele is in homozygous form compared to the average seed size in the fruits of plants comprising the wild type Ts-allele in homozygous form. To compare the average seed size of a plant comprising the mutant allele in homozygous form to a plant comprising the wild type allele in homozygous form, both plants preferably comprising the same seed size haplotype on chromosome 6, i.e., both comprise the S, M or L haplotype for chromosome 6.

Reduced expression or no expression of a mutant ts-allele means that there is a mutation in a regulatory region of the Ts-gene, such as the promoter, whereby reduced mRNA transcript or no mRNA transcript of the ts-allele is being made, compared to plants and plant parts comprising a wild type Ts-allele. The decrease in the expression can, for example, be determined by measuring the quantity of mRNA transcripts encoding Ts-protein, e.g., using Northern blot analysis or RT-PCR. For example the mutant allele may result in a reduction in the amount of mRNA transcripts by at least 10%, 20%, 30%, 40%, 50%, in particular by at least 60% or 70%, optionally by at least 80% or 85% or by at least 95%, or even by 100% compared to the plant or plant part comprising a wild type Ts-gene. Such a mutant allele may comprise a mutation in the regulatory sequence, e.g., in the promoter. The expression can be easily measured by e.g., measuring the amount of mRNA/cDNA being produced, e.g., in the fruit flesh during fruit development. The cDNA sequences encoding the Ts-protein of SEQ ID NO: 1 is depicted in SEQ ID NO: 3. The expression of cDNA sequences encoding functional variants comprising at least 90% sequence identity to SEQ ID NO: 1 can equally be analyzed and/or the expression quantified. The mutant allele will thus result in a reduced amount of wild type Ts-protein (of SEQ ID NO: 1 or a functional variant protein comprising at least 90% identity to SEQ ID NO: 1) being made in the plant or even no wild type Ts-protein being made. Therefore, also the amount of wild type Ts-protein being made can be measured in the plant or plant part and compared to the control plant or plant part (comprising the wild type allele).

As mentioned, in one aspect, the Ts-protein comprises one or more amino acids replaced, inserted or deleted compared to the wild type protein and is, therefore, referred to as 'mutant Ts-protein'. Thus, for watermelon, one or more amino acids are inserted, deleted or replaced compared to the wild type Ts protein of SEQ ID NO: 1 or compared to a wild type (functional variant) Ts-protein comprising at least 90%, 91%, 92%, 93%, 94%, 95%, 96%, 97% or 98% sequence identity to SEQ ID NO: 1, whereby the mutant protein has reduced function or loss of function compared to the wild type protein and thus results in a reduction in average seed size when the mutant allele is present in homozygous form in a diploid watermelon plant, compared to a diploid plant homozygous for the wild type allele.

It is for example disclosed herein that the replacement of amino acid 204 of SEQ ID NO: 1 (D204), or the equivalent amino acid in a sequence comprising at least 90%, 91%, 92%, 93%, 94%, 95%, 96%, 97% or 98% sequence identity to SEQ ID NO: 1, leads to a reduced function Ts-protein.

An "equivalent amino acid" in a protein comprising at least 90% sequence identity to the wild type Ts protein can be easily identified by aligning the two protein sequences pairwise (e.g. using the program Needle). The equivalent amino acid of the D204 of SEQ ID NO: 1 may for example be at position 205 or 203 in a sequence comprising at least 90% sequence identity to SEQ ID NO: 1.

An effect on reducing protein function, or abolishing protein function, may be seen for a replacement of any one or more amino acid of the wild type Ts protein, or for mutant proteins having one or more amino acids inserted or deleted compared to the functional Ts protein. As mentioned, the effect on protein function can be analyzed in vivo, in plants homozygous for the mutant allele.

In one aspect one or more amino acids of the wild type Ts-protein are replaced by one or more disfavourable amino acids in the mutant protein, reducing the function of the mutant protein. In one aspect the replacement of one or more amino acids by disfavourable amino acids is outside of the Acetyl transferase domain, so that the Acetyl transferase domain remains functional. In another aspect the replacement of one or more amino acids by disfavourable amino acids is within the Acetyl transferase domain, so that the Acetyl transferase domain becomes non-functional.

In one aspect the predicted effect of the mutant protein on protein function can be analyzed by determining the 3-dimensional predicted structure of the wild type and of the mutant protein e.g. by RaptorX Contact Prediction, to see if the predicted structure is changed. Ultimately, the effect of the mutant allele on the phenotype conferred by the gene should be determined, preferably in watermelon lines having similar genetic backgrounds (such as near isogenic lines).

Preferably, the phenotype regarding seed size is compared in plants having a genetic background whereby the seed size haplotypes for chromosome 6 are identical, either S, M or L, so that the effect of the mutant allele on chromosome 2 is not influenced by the haplotype on chromosome 6.

The N-acetyltransferases (NAT) (EC 2.3.1.-) are enzymes that use acetyl coenzyme A (CoA) to transfer an acetyl group to a substrate. In one aspect, the wild type Ts protein comprises a conserved Acetyl transferase domain (Pfam domain PF00583, Acetyltransf_1), i.e., a domain comprising 95%, 96%, 97%, 98%, 99% or 100% amino acid identity to amino acids 54 to 146 of SEQ ID NO: 1. Thus, in one aspect, the wild type Ts-gene encodes a wild type Ts-protein comprising a Acetyl transferase domain which is 95%, 96%, 97%, 98%, 99% or 100% identical to amino acids 54 to 146 of SEQ ID NO: 1.

In one aspect, the mutant ts-allele comprises a mutation whereby one or more amino acids in said Acetyl transferase domain are replaced, inserted or deleted. As the Acetyl transferase domain is required for the in vivo N-acetyltransferase function of the protein, any amino acid insertion, replacement or deletion will likely reduce or abolish the proper in vivo function of the protein, as can be verified by determining e.g., the phenotype (average seed size) as described herein.

Regarding mutations in the conserved Acetyl transferase domain (or in other parts of the protein), in one aspect especially mutations which lead to amino acid replacements, whereby the properties of the wild type amino acid and the replaced amino acid are different, e.g. replacement by disfavoured amino acids, are one aspect herein, as such different amino acid properties will reduce or abolish the proper protein folding (resulting in e.g. a deviant 3-dimensional structure from the wild type) and/or the normal function of the protein or of the domain. So, for example a replacement of a non-polar amino acid by a polar amino acid (comprising a hydrophilic side chain), or vice versa, or the replacement of an amino acid having a charged side chain with a non-charged or differently charged side-chain.

Thus, in one aspect any one (or more) of the amino acids of the conserved Acetyl transferase domain are replaced by one or more disfavored amino acids. The resulting mutant allele can then be tested for its predicted 3-dimensional structure and/or for its function by generating a plant homozygous for the mutant allele and analysing the phenotype.

In another aspect any one (or more) of the amino acids outside of the conserved Acetyl transferase domain are replaced by one or more disfavored amino acids. The resulting mutant allele can then be tested for its predicted 3-dimensional structure and/or for its function by generating a plant homozygous for the mutant allele and analysing the phenotype.

When amino acids "from' one amino acid "to" another amino acid are mentioned herein this includes the start/first and end/last amino acid mentioned.

In another aspect, the Ts protein comprises one or more amino acids inserted, replaced or deleted compared to the wild type Ts-protein, whereby the mutant Ts-protein has reduced function or a loss of function, whereby the amino acid insertion, replacement or deletion is in the N-terminal part of the protein, from amino acid 6 to 180, or from amino acid 4 to 371, or from amino acid 4 to 154, or from amino acid 54 to 146, or from amino acid 1 to 300, or from amino acid 1 to 250, or from amino acid 1 to 154 of SEQ ID NO: 1, or the equivalent amino acid(s) in a variant protein comprising at least 90% sequence identity to SEQ ID NO: 1. The N-terminal part of the protein appears to be the conserved part of the protein, required for in vivo function. For example, from amino acid 4 to 371 several helix structures and beta sheets are present in the 3-dimensional structure of the protein, more particularly from amino acid 4 to 154 (comprising the Acetyl transferase domain from amino acid 54 to 146) such 3-dimensional structures are present, which indicates that the N-terminal part plays a significant role in the functionality.

In one aspect, the insertion, deletion and/or replacement of one or more amino acids is predicted by e.g., Provean analysis to result in reduced or abolished protein function, i.e., the Provean analysis can be used to predict if the insertion, replacement or deletion has a "deleterious" effect. In one aspect, the insertion, deletion and/or replacement of one or more amino acids is predicted by 3-dimensional structure prediction to result in a deviant 3-ensional structure and/or a reduced or abolished protein function.

However, also the insertion, replacement or deletion of one or more amino acids in other parts of the Ts-protein can reduce the in vivo function or even abolish the in vivo function. This is illustrated by the mutant Ts-protein in which amino acid 204 is replaced, resulting in a reduced in vivo function of the protein.

In one aspect it is preferred that the plant comprises a mutant ts-allele, whereby some Ts-protein function remains in the plant, so that average seed size is reduced compared to the plant which is homozygous for the wild type allele, but seed size is larger than in a plant which is homozygous for a knock-out or deletion of the ts-allele or a mutant allele encoding a non-functional Ts-protein.

To achieve the presence of some Ts-protein function in the plant (thus, a reduced Ts-protein function but not an abolished function), either gene expression of the mutant allele may be reduced compared to the wild type allele or the encoded mutant Ts-protein may have reduced function compared to the wild type protein. So for example the mutant allele is modified in the promoter so that gene expression is equal to or less than 90%, 80%, 70%, 60%, 50% or 40%, 30%, 20% or 10% of the wild type level of gene expression. Or the mutant allele encodes a mutant protein which has some functionality in vivo, i.e. a reduced function Ts-protein.

In one aspect a reduced function Ts-protein comprises an intact/functional (wild type) Acetyl transferase domain (e.g. having an amino acid sequence identical to the Acyl transferase domain in the wild type protein, from amino acid 54 to 146 of SEQ ID NO: 1), but it has a reduced in vivo function due to one or more amino acids being inserted, deleted and/or replaced outside of the Acetyl transferase domain, e.g. any amino acid starting at amino acid 147 and ending at amino acid 412, or starting at amino acid 147 and ending at amino acid 400, or starting at amino acid 150 and ending at amino acid 390, especially starting at amino acid 155 and ending at amino acid 265. Replacement one or more (e.g. 2, 3, 4, 5) amino acids in the middle region of the Ts protein, i.e. from amino acid 155 to 265 of SEQ ID NO: 1 (or the equivalent amino acids in a protein comprising at least 90% sequence identity to SEQ ID NO: 1) is likely to reduce protein function without abolishing the function altogether. The mutant protein in one aspect comprises one or more amino acid replacements whereby amino acids are replaced with disfavoured amino acids, such as a polar amino acid being replaced by a non-polarpolar amino acid. For example, D (Asp) is a polar amino acid, which may be replaced by Y (Tyr), which is another polar amino acid.

FIG. 6 shows a 3-dimensional structure of the wild type, functional Ts-protein, with D204 (which is present in the middle domain of the protein) highlighted. The N-terminal domain contains the conserved Acetyl transferase domain.

In a specific aspect, amino acid 204 of SEQ ID NO: 1, or the equivalent amino acid of a functional variant of SEQ ID NO: 1 (i.e., a functional Ts protein comprising at least 90% sequence identity to SEQ ID NO: 1), is deleted or replaced by a different amino acid, rendering the mutant Ts-protein to have a reduced function. In one aspect, D204 (Asp 204) is replaced by Y (Tyr) or by another polar amino acid. In a further aspect, D204 (Asp 204) is replaced by any amino acid, except for Y (Tyr), e.g., by N (Asn), H (His), V (Val), G (Gly), A (Ala) or E (Glu).

Thus, in one aspect the plant, plant part or plant cell comprises a mutant allele of the is-gene, whereby the above amino acid insertions, replacements or deletions are encoded by the allele.

In yet another aspect, the mutant Ts-protein comprises one or more amino acids deleted compared to the wild type Ts-protein, whereby the mutant protein has reduced function or a loss of function. For example, the mutation may lead to a premature STOP codon in the coding sequence and/or to a frame shift in the coding sequence or to a splice variant, whereby one or more amino acids are deleted. The mutant allele may thus encode e.g., a truncated Ts-protein, whereby part of the C-terminal (the end of the protein) is deleted. In one aspect, the mutant allele encodes a mutant Ts protein lacking at least 30, 40, 50, 60, 70, 80, 90, 100 or more of the C-terminal amino acids of SEQ ID NO: 1 or of a functional variant protein comprising at least 90% sequence identity to SEQ ID NO: 1. A frame-shift mutation may also result in a truncated Ts-protein. Even if certain amino acids of the wild type protein are replaced by other amino acids due to the frame shift, the protein is still regarded as being truncated, as the wild type amino acids are not present following the frame shift.

Also encompassed herein are mutant alleles, wherein all or part of the wild type Ts-allele is deleted, e.g., all or part of the genomic sequence, all or part of the promoter sequence or other regulatory elements, or even the entire allele may be deleted. In one aspect, SEQ ID NO: 8 is deleted. In another aspect, the deletion is not the deletion of SEQ ID NO: 8, but a different deletion comprising the Ts-allele, preferably a smaller deletion of genomic DNA comprising all or part of the Ts-allele. The large deletion in the original Sugar Baby mutant is almost 14000 bases (as shown in SEQ ID NO: 8) and contained maybe other genes or other genomic DNA which is preferably not deleted along with the Ts-gene, or with part of the Ts-gene. The genomic sequence of the Ts-gene is 1982 (SEQ ID NO: 2) bases long. The upstream regulatory elements, such as the promoter, are present in the 1000 to 2000 base region upstream of the genomic sequence. Thus, in one particular aspect, the deletion of all or part of the Ts-allele is any deletion, but not the same deletion as present in the original Sugar Baby mutant and as present in variety WH9716, i.e., it is not the deletion of SEQ ID NO: 8, but a different deletion. A deletion of all or part of the Ts-allele can for example be generated by Crispr based methods or other targeted genome editing methods such as TALEN. In Liu, Y., Gao, Y., Gao, Y. et al. (Targeted deletion of floral development genes in *Arabidopsis* with CRISPR/Cas9 using the RNA endoribonuclease Csy4 processing system. Hortic Res 6, 99, 2019) specific exons were deleted, leading to loss-of-function mutations. Such deletions are encompassed herein for the Ts-allele, whereby all or part of the allele is deleted, resulting in no functional Ts protein being made anymore.

In another aspect, an insertion of DNA into the Ts-allele is encompassed, rendering the Ts-allele to have reduced expression or no expression compared to the wild type allele or rendering the encoded Ts-protein to have reduced function or no function. For example, a transposable element inserted into the allele can render the allele to be a knock out allele, but also targeted genome editing can insert nucleotides into the allele.

In one aspect, a mutant ts-allele as described herein, or the deletion of all or part of the Ts-allele as described herein, is heterozygous in a diploid watermelon plant cell, plant part or plant or seed, i.e., only one chromosome 2 comprises the mutant allele or the deletion. In another aspect, the mutant ts-allele, or the deletion of all or part of the Ts-allele, is homozygous in a diploid plant cell, plant part or plant or seed, i.e., both chromosomes 2 comprise the mutant allele or the deletion.

The plant cells, parts and plants are preferably cultivated plants, such as elite breeding lines or varieties, and not wild plants. The watermelon plant may be any type of watermelon plant. In a preferred aspect, it is an inbred watermelon line, which e.g., can be used as a parent line to make F1 hybrid watermelon seeds and F1 hybrid plants that can be grown from the seeds. In a further aspect, F1 hybrid watermelon seeds comprising at least one copy of a mutant ts-allele (or the deletion of all or part of the Ts-allele) are also an embodiment herein. Preferably, the F1 hybrid seeds and plants comprise two copies of a mutant ts-allele (or the deletion of all or part of the Ts-allele on both chromosomes) as described herein.

Watermelon plants, and parts thereof, which comprises at least one copy of the mutant ts-allele, or a deletion of all or part of the Ts-allele, may be diploid, tetraploid or triploid. A tetraploid plant comprising, in one aspect, four copies of the mutant ts-allele or of the deletion of all or part of the Ts-allele, and a triploid plant three copies.

In one aspect, the diploid plant comprising the mutant ts-allele (or the deletion of all or part of the Ts-allele) in homozygous form is a double haploid plant (DH), e.g., a double haploid watermelon plant or plant cell or plant part.

Seeds from which any of the watermelon plants described can be grown are also encompassed herein, as are parts of such a plant, such as fruits, flowers, cells, roots, rootstocks, scions, leaves, stems, vegetative propagations, cuttings, seed propagations (e.g., selfings) and also in vitro cell- or tissue cultures, as well as pollen, ovaries, etc. are encompassed herein.

The mutant ts-allele, or the deletion of all or part of the wild type Ts-allele, may be present in a watermelon plant in combination with any of the chromosome 6 haplotypes described herein, i.e., either with the Small, Medium or Large haplotype for chromosome 6. Preferably, the mutant ts-allele (or the deletion of all or part of the wild type Ts-allele) and the chromosome 6 haplotype are both in homozygous form. Thereby, any of the combinations of the chromosome 2 haplotype 'NO' or 'RE' of FIG. 2 (and Table 1) with chromosome 6 haplotypes S, M and L (of FIG. 2 or Table 2) are possible.

Plants comprising the mutant ts-allele, or the deletion of all or part of the wild type Ts-allele, according to the disclosure may thus be used in the seed size prediction models and methods for identification and/or selection of plants described elsewhere herein and illustrated in FIGS. 2 and 3. In those methods, the original deletion of SEQ ID NO: 8, or plants comprising the deletion, may be used. The original Sugar Baby ts-mutant plant comprises the deletion of SEQ ID NO: 8 in homozygous form and comprises the 'S' haplotype for chromosome 6 (i.e., SEQ ID NO: 4 and SEQ ID NO: 6) in homozygous form. The hybrid WH9716 comprises the deletion of SEQ ID NO: 8 in homozygous form and comprises the 'M' haplotype for chromosome 6 (i.e., SEQ ID NO: 4 and SEQ ID NO: 7) in homozygous form. Likewise, the D204Y ts-mutant allele, or plants comprising this allele, or other mutant ts-alleles described herein, may be used in the seed size prediction models and methods for identification and/or selection of plants described elsewhere herein and illustrated in FIGS. 2 and 3. The variety SP-4 comprises the D204Y ts-mutant allele on chromosome 2 in homozygous form and comprises 'S' haplotype for chromosome 6 (i.e., SEQ ID NO: 4 and SEQ ID NO: 6) in homozygous form.

Variety SP-4 is a commercial pollinizer described in e.g. U.S. Pat. No. 7,550,652B2. Obviously, the same or other ts-mutant alleles can be generated de novo as described herein.

As the fruits produced on plants which are homozygous for the mutant ts allele (or deletion of all or part of the Ts-allele) produce significantly smaller seeds than the fruits of plants which are homozygous for the wild type Ts-allele, such fruits and parts of fruits (e.g., cut pieces) are also an embodiment herein. Fruits may be harvested, optionally placed in containers or packages. Fruits may also be processed. The fruits and parts thereof can be easily distinguished by the presence of the mutant ts-allele (or the deletion of all or part of the Ts allele) in their genomic DNA. So the DNA of e.g., the fruit flesh may be analyzed for the presence of the mutant ts-allele (or the deletion of all or part of the Ts allele). Fruits may be processed, e.g., cut, sliced, cubed, etc. for e.g., fresh consumption. Thus, also parts of fruits are encompassed herein.

Also fruits of plants heterozygous for a mutant ts-allele (or the deletion of all or part of the Ts allele) as described herein are an aspect of the disclosure.

Likewise, plant parts comprising at least one copy of a mutant ts-allele (or the deletion of all or part of the Ts allele) are encompassed herein, such as a cell, a flower, a leaf, a stem, a cutting, an ovule, pollen, a root, a rootstock, a scion, a fruit, a protoplast, an embryo, an anther.

In a further aspect, a vegetatively propagated plant propagated from a plant part according to the disclosure is provided.

Also propagating and non-propagating cells comprising at least one copy of a mutant ts-allele (or the deletion of all or part of the Ts allele) are provided herein. It is understood that such propagating or non-propagating cells can be part of a plant organ or of an entire plant, or they can be isolated, e.g., in a cell culture or tissue culture. In one aspect, the term plant part refers to plant cells, or plant tissues or plant organs that comprise one or more of the mutant ts-alleles (or the deletion of all or part of the Ts allele) described herein. In one aspect a plant part can grow into a plant and/or live on photosynthesis (i.e., synthesizing carbohydrate and protein from the inorganic substance, such as water, carbon dioxide and mineral salt). In another aspect, a plant part cannot grow into a plant and/or live on photosynthesis (i.e., synthesizing carbohydrate and protein from the inorganic substance, such as water, carbon dioxide and mineral salt). Thus, a plant part can be propagating or non-propagating.

Apart from watermelon plants and plant parts comprising a mutant ts-allele, also methods for generating mutations in the Ts-gene and methods for identifying or selecting plants comprising a mutant ts-allele are encompassed herein.

In one aspect a method for modifying the endogenous Ts-gene on chromosome 2 of the watermelon genome is provided, comprising using a targeted gene editing method, such as a Crispr based method, to introduce mutations, such as nucleotide additions or deletions, into the endogenous Ts-allele and selecting plants comprising the mutant Ts-allele, wherein the endogenous Ts-gene is the gene encoding the protein of SEQ ID NO: 1 or a protein comprising at least 90% sequence identity to SEQ ID NO: 1.

In another aspect a method for modifying the endogenous Ts-gene on chromosome 2 of the watermelon genome is provided, comprising using a random mutagenesis method, such as treatment of seeds or plant parts with a mutagenic chemical agent or mutagenic radiation, to introduce mutations, such as nucleotide additions or deletions, into the endogenous Ts-allele and selecting plants comprising the mutant Ts-allele, wherein the endogenous Ts-gene is the gene encoding the protein of SEQ ID NO: 1 or a protein comprising at least 90% sequence identity to SEQ ID NO: 1.

A further embodiment of the disclosure concerns a method for production of a plant comprising the steps of a) providing a mutated or genetically modified plant (or seed) or a population of mutated or genetically modified watermelon plants (or seeds), b) determining if a plant (or seed) of a) has a mutation in an allele of a Ts protein-encoding gene (i.e., comprises a mutant ts-allele) and/or comprises a deletion of all or part of the wild type Ts allele, optionally c) growing/cultivating the plants obtained under b).

In one aspect, the disclosure provides a method for production of a plant comprising the steps of a) introducing mutations or genetic modifications in a plant (or seed) or in a population of plants (or seeds) and optionally selfing the plants, b) determining if the plant (or seed) under a) has a mutation in an allele encoding a Ts protein-encoding gene (i.e., comprises a mutant ts-allele) and/or comprises a deletion of all or part of the wild type Ts allele and selecting a plant comprising such a mutant allele or deletion of all or part of the allele, and optionally c) growing/cultivating the plants obtained under b).

Mutations can be introduced by e.g., chemical or radiation treatment or genome editing techniques. Other genetic modifications may be introduced by targeted gene editing techniques, such as Crispr based techniques.

The mutant allele in one aspect encodes a mutant Ts-protein, comprising reduced function or loss of function, whereby the plant homozygous for the mutant Ts-allele produces in its fruits seeds having an average seed size which is significantly smaller than the average seed size produced in fruits of plants which are homozygous for the wild type Ts-allele.

Any method for mutating or genetically modifying or targeted genome editing of the Ts-gene is encompassed herein.

However, in one aspect, the order of the steps can also be different, comprising:

a) providing a mutant plant (or seed) or a population of mutant plants (or seeds) or a genetically modified plant (or seed) or a population of genetically modified plants (or seeds), b) determining if a plant (or seed) of a) has a mutation in an allele of a Ts protein-encoding gene (i.e., comprises a mutant ts-allele) and/or comprises a deletion of all or part of the wild type Ts allele, optionally c) selecting a plant comprising a mutation in an allele of a Ts-protein encoding gene (i.e., comprises a mutant ts-allele) and/or comprises a deletion of all or part of the wild type Ts allele, and optionally d) selfing the plant of b) or c) to generate a plant comprising the mutant allele or the deletion in homozygous form, and optionally e) determining the average seed size produced in the fruits of the plant of step c) or d).

Or the steps may comprise:

a) introducing mutations in a population of plants (or seeds) (and optionally selfing the plants)

b) determining if a plant (or seed) of a) has a mutation in an allele encoding a Ts protein-encoding gene (i.e., comprises a mutant ts-allele) and/or comprises a deletion of all or part of the wild type Ts-allele and, optionally, c) selecting a plant comprising such a mutation or deletion, and optionally d) selfing the plant of b) or c) to generate a progeny plant comprising the mutant allele or deletion in homozygous form, and, optionally, e) determining the average seed size produced in the fruits of the plant of step c) or d).

Also provided is a method of targeted gene editing of the endogenous Ts-gene of watermelon, comprising generating one or more nucleotide insertions, deletions or replacements in the endogenous watermelon Ts-allele, e.g. in the promoter sequence or the coding sequence. This can for example be done by targeted gene editing methods, such as Crispr based methods, whereby the Ts-gene is the target gene. The Crispr construct is removed/crossed out after editing and the non-gmo progeny plant comprising the mutant ts-allele is selected and optionally used in further breeding.

Furthermore a method of generating and/or identifying a plant comprising a mutant allele of the endogenous Ts-gene of watermelon is provided, comprising generating one or more nucleotide insertions, deletions or replacements in the endogenous watermelon Ts-allele, e.g. in the promoter sequence or the coding sequence, by mutagenesis techniques (such as treatment of plants or parts with radiation or chemical agents to induce random mutations). This can for example be done by treating seeds with a mutagenic agent and identifying progeny plants/seeds comprising a mutant ts-allele.

In a different aspect, a method of producing watermelon fruits comprising at least one copy of a mutant ts-allele (or the deletion or all of part of the Ts-allele), preferably two copies, is provided said method comprising growing a watermelon plant comprising the mutant allele (or the deletion of all or part of the Ts-allele) and optionally harvesting the fruits produced by said plants.

A method for generating a watermelon plant comprising a mutant allele of a gene named Ts-gene, or a deletion of all or part the Ts-gene, is provided, said Ts-gene encodes a Ts-protein of SEQ ID NO: 1 or a protein comprising at least 90%, 91%, 92%, 93%, 94%, 95%, 96%, 97%, 98% or 99% sequence identity to SEQ ID NO: 1, comprising identifying and/or selecting a mutant plant from e.g., a population of mutant plants, or progeny thereof obtained by selfing, comprising a mutant Ts-gene allele or a deletion of all or part the Ts-gene, or generating a watermelon plant comprising a mutant Ts-gene allele using a genome editing technique.

A method for determining whether a watermelon plant or plant part comprises at least one copy of a mutant allele of a gene named Ts-gene or a deletion or all of part of the Ts-gene, is provided, said Ts-gene encodes a Ts-protein of SEQ ID NO: 1 or a protein comprising at least 90%, 91%, 92%, 93%, 94%, 95%, 96%, 97%, 98% or 99% sequence identity to SEQ ID NO: 1, said method comprising analyzing the genomic DNA sequence, gene expression or protein amount or amino acid sequence of the Ts-gene of the plant or plant part.

A method of using the nucleotide sequence (e.g., all or part of the genomic sequence or molecular markers linked thereto or all or part of the mRNA/cDNA sequence) or protein sequence of the Ts-gene, said Ts-gene encodes a Ts-protein of SEQ ID NO: 1 or a protein comprising at least 90%, 91%, 92%, 93%, 94%, 95%, 96%, 97%, 98% or 99% sequence identity to SEQ ID NO: 1, in selecting watermelon plants or plant parts.

As the sequences of the Ts-gene are now disclosed and the location on chromosome 2 is disclosed, these sequences can be used in breeding of watermelon plants, such as marker assisted selection of Ts alleles (wild type or mutant alleles). Therefore, also a method for using the Ts-gene, or any markers physically linked thereto, in breeding, e.g., in marker assisted selection, is provided herein.

A method for selection a watermelon plant or plant part comprising a) detecting the presence of a wild type Ts allele or a mutant ts-allele or a deletion of all or part of the Ts allele and b) selecting the plant based on step a). This can be done by e.g., method which are commonly used to detect alleles, such as molecular markers linked to an allele or markers within an allele or DNA differences between the alleles and the like. Thus, allele specific detection methods can easily be developed by the skilled person.

The disclosure also provides for the use of any of SEQ ID NO: 1, 2, 3 and/or 8 or a sequence comprising at least 90%, 91%, 92%, 93%, 94%, 95%, 96%, 97%, 98% or 99% sequence identity to any one of SEQ ID NO: 1, 2, 3 and/or 8 for selecting a plant or plant line or plant part.

Likewise, the disclosure provides for the use of any of the chromosome 6 markers, i.e., SEQ ID NO: 4 and/or 5 (SNP_01) and/or SEQ ID NO: 6 and/or 7 (INDEL marker) or a sequence comprising at least 90%, 91%, 92%, 93%, 94%, 95%, 96%, 97%, 98% or 99% sequence identity to any one of SEQ ID NO: 4, 5, 6 or 7 for selecting a plant or plant line or plant part are an embodiment herein. These markers can be used to select and/or determine the chromosome 6 haplotype of a watermelon plant or plant part.

In one aspect, a method for identifying a plant or plant part or cell comprising in its genome at least one copy of a mutant allele of Ts-gene or a deletion of all or part of the Ts-allele is provided, said method comprising
determining whether the plant or plant part or cell comprises in its genome at least one mutant ts-allele (or a deletion of all or part of the Ts-allele).

This method may involve analyzing (directly or indirectly) the gene expression of the ts-allele, and/or the genomic nucleotide sequence of the ts-allele or linked to the ts-allele, or the mRNA nucleotide sequence of the ts-allele or the mRNA amount (expression), or the protein sequence of the Ts protein, or the protein amounts of the Ts protein of the plant or plant part or plant cell, to determine if the gene expression is knocked down or knocked out compared to the wild type plant or plant part or plant cell, or if the encoded protein comprises one or more amino acid insertions, deletions or replacements compared to the wild type Ts protein, or if all or part of the wild type Ts-allele is deleted.

One method for analyzing the presence of a mutant ts-allele, is for example to assay the presence of a Single Nucleotide Polymorphism (SNP) in the genomic sequence of the ts-allele, by, for example, designing primers for the SNP and genotyping plants or plant parts for the genotype of that particular SNP. For example, in the Examples a KASP assay for the Single Nucleotide Polymorphism that changes the wild type codon 'GAC' (coding for D, Asp, at amino acid 204 of SEQ ID NO: 1) into codon 'TAC' (coding for Y, Tyr at amino acid 204 of SEQ ID NO: 1) can be used to detect the mutant ts-allele, which encodes the mutant Ts protein comprising a Tyrosine at amino acid 204 and having reduced function compared to the wild type Ts protein.

A method for detecting the presence of a ts-allele encoding the mutant Ts protein comprising a different amino acid than Asp (D) at amino acid 204 of SEQ ID NO: 1 in a watermelon plant or plant part is therefore also an embodiment herein. The different amino acid may be Tyr (Y).

Similarly, the absence in the genome of all or part of the wild type Ts-allele can be analyzed by determining the presence or absence of all or part of any of SEQ ID NO: 1, SEQ ID NO: 2, SEQ ID NO: 3, and/or SEQ ID NO: 8, or a sequence comprising at least 90%, 91%, 92%, 93%, 94%, 95%, 96%, 97%, 98% or 99% sequence identity to SEQ ID NO: 1, SEQ ID NO: 2, SEQ ID NO: 3 or SEQ ID NO: 8.

Optionally, a plant is selected which lacks all or part of the wild type Ts-allele in its genome. Such a plant is also an embodiment hereon.

In one aspect, a method for identifying and/or selecting a plant or plant part or cell comprising in its genome a deletion of all or part of the Ts-gene, is provided, said method comprising determining the absence of all or part of any of SEQ ID NO: 1, SEQ ID NO: 2, SEQ ID NO: 3 and/or SEQ ID NO: 8, or a sequence comprising at least 90%, 91%, 92%, 93%, 94%, 95%, 96%, 97%, 98% or 99% sequence identity to SEQ ID NO: 1, 2, 3 or 8.

In one aspect, a method for identifying and/or selecting a plant or plant part or cell comprising in its genome at least one copy of a mutant allele of is gene, or a deletion of all or part of the Ts-gene, is provided, said method comprising
determining whether the plant or plant part or cell comprises in its genome at least one copy of a mutant allele of a gene named Ts-gene or a deletion or all of part of the Ts-gene, said Ts-gene encodes a Ts-protein of SEQ ID NO: 1 or a protein comprising at least 90%, 91%, 92%, 93%, 94%, 95%, 96%, 97%, 98% or 99% sequence identity to SEQ ID NO: 1, wherein the mutant allele of the Ts-gene or the deletion of all or part of the Ts-gene results in reduced or no expression of the Ts-gene compared to the wild type Ts-gene or results in a mutant Ts-protein being made having reduced function or no function compared to the wild type Ts-protein.

In one aspect, a method for identifying and/or selecting a plant or plant part or cell comprising in its genome at least one copy of a mutant allele of the Ts-gene is provided, said method comprising
determining whether the plant or plant part or cell comprises in its genome at least one mutant ts allele, wherein the mutant ts allele encodes a different amino acid than the wild type Asp at amino acid 204 of SEQ ID NO: 1 or wherein the encoded protein lacks at least amino acid 204. Optionally, other amino acids may be lacking, such as one or more amino acids following and/or preceding amino acid number 204.

Thus, one aspect of the disclosure comprises a method for determining whether a plant, plant part or plant cell comprises one or more copies of a mutant ts-allele by a method selected from analyzing one or more nucleotides of the genomic ts-allele in a genotyping assay, analyzing the mRNA (or cDNA) expressed by the ts-allele or analyzing the Ts protein amount and/or amino acid sequence (using e.g., antibody based detection).

Isolated proteins and isolated nucleotide molecules of any of SEQ ID NO: 1, 2, 3 and/or 8 or a sequence comprising at least 90%, 91%, 92%, 93%, 94%, 95%, 96%, 97%, 98% or 99% sequence identity to any one of SEQ ID NO: 1, 2, 3 and/or 8 are provided herein, as are fragments thereof. For example, PCR primers which amplify all or part of the ts-allele and/or detection kits comprising such primers.

In one aspect the plants, plant parts and plant cells according to the invention are not exclusively obtained by means of an essentially biological process as defined by Rule 28 (2) EPC (European Patent Convention).

In one aspect the plants are non-GMO (not genetically modified).

In one aspect the mutant alleles are generated by mutagenesis (e.g. chemical or radiation mutagenesis) or by targeted mutagenesis, especially using the CRISPR system (e.g. Crispr/Cas9 or Crispr/Cpf1 or other nucleases). In one aspect the cultivated plant comprising the mutant ts-allele is not a transgenic plant, i.e. non transgenic progeny are selected which do not comprise e.g. the CRISPR construct.

In one aspect the mutant allele of the Ts gene comprises a human induced mutation, i.e. a mutation introduced by mutagenesis techniques, such as chemical mutagenesis or radiation mutagenesis, or targeted mutagenesis techniques, such as Crispr based techniques.

A method for targeted mutagenesis of the endogenous Ts gene in watermelon is provided herein, using any targeted gene modification method, such as CRISPR based methods (e.g. Crispr/Cas9 or Crispr/Cpf1), TALENS, Zinc Fingers or other methods.

In one aspect an isolated mutant Ts protein and an isolated wild type Ts protein is provided or an isolated nucleic acid molecule encoding a mutant Ts protein or a wild type Ts protein. Also an antibody able to bind a mutant or wild type Ts protein is encompassed herein.

Further Detection Methods:

In one aspect a screening method for identifying and/or selecting seeds, plants or plant parts or DNA from such seeds, plants or plant parts comprising in their genome a mutant allele of a Ts protein-encoding gene or a wild type allele of the Ts-gene or a deletion of all or part of the Ts-gene is provided.

The method comprises screening at the DNA, RNA (or cDNA) or protein level using known methods, in order to detect the presence of the mutant allele or of the wild type allele or to detect the deletion of all or part of the Ts-allele. There are many methods to detect the presence of a mutant allele of a gene or of a wild type allele of a gene or of the deletion of all or part of the gene.

Thus, a method for screening and/or selecting plants or plant material or plant parts, or DNA or RNA or protein derived therefrom, for the presence of a mutant is allele, or for the presence of a wild type Ts-allele, or for the presence of a deletion of all or part of the Ts-allele, is provided comprising one or more of the following steps:

a) determining the gene expression of the endogenous Ts gene, e.g. to determine if it is reduced or abolished;
b) determining the amount of wild type Ts protein, e.g. to determine if it is reduced or abolished;
c) determining if a mutant or if a wild type mRNA, cDNA or genomic DNA encoding a mutant or wild type Ts protein is present;
d) determining if a mutant Ts protein is present and/or of a wild type Ts protein is present;
e) determining if plants or progeny thereof produce fruits having seeds with a (average) smaller seeds size than the plants homozygous for the wild type Ts-allele;
f) determining whether chromosome 2 lacks all or part of the Ts-gene.

Routine methods can be used, such as RT-PCR, PCR, antibody based assays, sequencing, genotyping assays (e.g. allele-specific genotyping), phenotyping, etc.

The plants or plant material or plant parts may be watermelon plants or plant materials or plant parts, such as leaves, leaf parts, cells, fruits, fruit parts, ovaries, stem, hypocotyl, seed, parts of seeds, seed coat, embryo, etc.

For example if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP-assay method. Equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Based on the difference between the genomic sequence of the wild type allele and the mutant allele, the skilled person can easily develop markers which can be used to detect specific alleles.

Also provided herein is a method for identifying a watermelon plant (or plant part) comprising a mutant is allele, the method comprising detecting in the plant (or plant part) the presence of a mutant ts allele, wherein the presence is detected by at least one marker within the ts allele or by detecting the protein encoded by the ts allele. The method for detecting the mutant ts allele is selected from the group consisting of PCR amplification, nucleic acid sequencing, nucleic acid hybridization and an antibody-based assay (e.g. immunoassay) for detecting the Ts protein encoded by the allele.

Also provided herein is a method for identifying a watermelon plant (or plant part) comprising a mutant ts allele comprising a mutation in a regulatory element, the method comprising detecting in the plant (or plant part) the reduced gene expression or absence of gene expression of the mutant ts allele, wherein the presence is detected by mRNA levels (cDNA) of the wild type Ts allele or by detecting the protein levels of the wild type Ts protein. The method for detecting the mutant ts allele is selected from the group consisting of PCR amplification (e.g. RT-PCR), nucleic acid sequencing, western blotting and an antibody based assay (e.g. immunoassay) for detecting the Ts protein encoded by the allele.

Also provided is a method for determining, or detecting or assaying, whether a cell or of a watermelon plant or plant part comprises a mutant allele of a gene name Ts gene encoding a protein of SEQ ID NO: 1, or a protein comprising at least 90%, 91%, 92%, 93%, 94%, 95%, 96%, 97% or 98% sequence identity to SEQ ID NO: 1, is provided herein. In one aspect the method comprises determining the expression of the allele, and/or determining the coding sequence of the allele and/or determining part of the coding sequence of the allele (e.g. a SNP genotype of the allele), and/or determining the amino acid sequence of the protein produced and/or the amount of protein produced.

Therefore provided is in one aspect a watermelon plant or plant part comprising at least one copy of a mutant allele of a gene named Ts-gene or comprises a deletion of all or part of the Ts-gene, said Ts-gene encodes a functional Ts-protein of SEQ ID NO: 1 or a protein comprising at least 90%, 91%, 92%, 93%, 94% or 95% sequence identity to SEQ ID NO: 1, wherein the mutant allele has reduced expression or no expression compared to the wild type allele of the Ts-gene, or wherein the mutant allele encodes a mutant Ts-protein having reduced functioned or loss of function compared to the wild type Ts-protein of SEQ ID NO: 1 or compared to a wild type Ts-protein comprising at least 90%, 91%, 92%, 93%, 94% or 95% sequence identity to SEQ ID NO: 1.

The watermelon plant or plant part as e.g. described above is provided, wherein the mutant allele of the Ts-gene encodes a reduced function Ts-protein comprising one or more amino acids inserted, deleted or replaced compared to the wild type protein of SEQ ID NO: 1.

In one aspect the watermelon plant or plant part as e.g. described above is provided wherein the mutant allele of the Ts-gene does not encode a mutant Ts-protein in which the Aspartic acid (D) at amino acid 204 of SEQ ID NO:1 is replaced by a Tyrosine (Y).

In one aspect the watermelon plant or plant part as e.g. described above is provided which does not comprise a deletion of SEQ ID NO: 8 but comprises a different deletion of all or part of the Ts-gene.

In one aspect the watermelon plant or plant part as e.g. described above is provided, wherein said plant is homozygous for said mutant allele of the Ts-gene or for the deletion of all or part of the Ts-gene.

In one aspect the watermelon plant or plant part as e.g. described above is provided, wherein said mutant allele of the Ts-gene is an induced mutant allele.

In one aspect the watermelon plant or plant part as e.g. described above is provided, wherein said mutant allele encodes a protein that is truncated compared to the wild type protein.

Also provided is a seed from which a plant or plant part as e.g. described above can be grown.

Also provided is a fruit produced by the plant e.g. described above, wherein said fruit preferably comprises said mutant allele in homozygous form.

Also provided is plant part according of a watermelon plant as e.g. described above, wherein the plant part is a cell, a flower, a pistil, a leaf, a stem, a petiole, a cutting, a tissue, a seed coat, an ovule, pollen, a root, a rootstock, a scion, a fruit, a cotyledon, a hypocotyl, a protoplast, an embryo, or an anther.

Also provided is a vegetatively propagated plant propagated from a plant part of a watermelon plant as e.g. described above.

Further provided is a method of crossing the plant as e.g. described above with another watermelon plant to produce a hybrid plant.

Further provided is a hybrid watermelon plant or a part thereof having the plant as e.g. described above as a parent and comprising at least one copy of the mutant allele of the is-gene.

Likewise a method of watermelon fruit production is provided, said method comprising growing a plant as e.g. described above comprising the mutant Ts-gene allele in homozygous form and optionally harvesting the fruits produced by said plants.

Further provided is a method for generating a watermelon plant comprising a mutant allele of a gene named Ts-gene, said Ts-gene encodes a Ts-protein of SEQ ID NO: 1 or a protein comprising at least 90%, 91%, 92%, 93%, 94% or 95% sequence identity to SEQ ID NO: 1, comprising identifying or selecting a mutant plant, for example from a population of mutant plants or progeny thereof obtained by selfing, comprising a mutant Ts-gene allele, or generating a watermelon plant comprising a mutant Ts-gene allele using a genome editing technique.

In another aspect a method for determining whether a watermelon plant or plant part comprises at least one copy of a mutant allele of a gene named Ts-gene is provided, said Ts-gene encodes a Ts-protein of SEQ ID NO: 1 or a protein comprising at least 90%, 91%, 92%, 93%, 94% or 95% sequence identity to SEQ ID NO: 1, said method comprising analyzing the Ts-gene DNA, RNA or protein of the plant or plant part.

In another aspect a method for selecting watermelon plants or plant parts is provided comprising screening the DNA, RNA or protein sequence of the Ts-gene or markers linked to the Ts-gene in said watermelon plants or plant parts, said Ts-gene encodes a Ts-protein of SEQ ID NO: 1 or a protein comprising at least 90%, 91%, 92%, 93%, 94% or 95% sequence identity to SEQ ID NO: 1, and selecting watermelon plants or plant parts.

Models for Predicting Seeds Size in Inbreds and Hybrids and Methods for Selecting Parent Lines and Making Hybrids It was found that there are three seed size determining haplotypes for the Ts-gene on chromosome 2 (referred to as haplotype 'NO', 'RE' and 'WT', as described above and shown e.g., in Table 1) and three seed size determining haplotypes on chromosome 6 (referred to as haplotype 'S', 'M' and as described above and shown in e.g., Table 2).

Based on the finding that parent lines homozygous for a particular haplotype on chromosome 2 and homozygous for a particular haplotype on chromosome 6 produced an actual average seed size in their fruits—which highly correlated (see FIG. 4) with the seed size predicted based on the chromosome 2 and 6 haplotype, the model being shown in FIG. 2—it is now possible to select watermelon lines on the basis of the chromosome 2 and chromosome 6 haplotype.

In addition, it was found that inbred parent lines which are selected based on the chromosome 2 and chromosome 6 haplotype can also be used as parent lines for F1 hybrid seed production, to produce F1 hybrid plants which produce an actual average seed size in their fruits which highly correlated (see FIG. 5) with the predicted average seed size, as shown in the model of FIG. 3. It is therefore now possible to select two inbred parent watermelon lines on the basis of the chromosome 2 and chromosome 6 haplotype, which when crossed produce F1 hybrid seeds, which when grown will produce fruits comprising a predicted average seed size.

In one aspect, the disclosure provides a method for selecting a watermelon plant which, when grown, produces in its fruits seeds of
  i) an average predicted seed weight falling within the range of 0.07 g/10 seeds to 0.26 g/10 seeds, comprising selecting a plant which
    a) does not produce a wild type, functional Ts-protein (chromosome 2 haplotype 'NO'), and
    b) is either homozygous for SEQ ID NO: 4 and SEQ ID NO: 6 (chromosome 6 haplotype Small), or is homozygous for SEQ ID NO: 4 and SEQ ID NO: 7 (chromosome 6 haplotype Medium), or is homozygous for SEQ ID NO: 5 and SEQ ID NO: 6 (chromosome 6 haplotype Medium), or is homozygous for SEQ ID NO: 5 and SEQ ID NO: (chromosome 6 haplotype Large); or
  ii) an average predicted seed weight falling within the range of 0.15 g/10 seeds to 0.61 g/10 seeds, comprising selecting a plant which
    a) produces a mutant Ts-protein having reduced function, or produces a reduced amount of wild type, functional Ts-protein (chromosome 2 haplotype 'RE'), and
    b) is either homozygous for SEQ ID NO: 4 and SEQ ID NO: 6 (chromosome 6 haplotype Small), or is homozygous for SEQ ID NO: 4 and SEQ ID NO: 7 (chromosome 6 haplotype Medium), or is homozygous for SEQ ID NO: 5 and SEQ ID NO: 6 (chromosome 6 haplotype Medium), or is homozygous for SEQ ID NO: 5 and SEQ ID NO: (chromosome 6 haplotype Large); or
  iii) an average predicted seed weight falling within the range of 0.27 g/10 seeds to 0.97 g/10 seeds, comprising selecting a plant which
    a) produces a wild type, functional Ts-protein (chromosome 2 haplotype 'WT'), and
    b) is either homozygous for SEQ ID NO: 4 and SEQ ID NO: 6 (chromosome 6 haplotype Small), or is homozygous for SEQ ID NO: 4 and SEQ ID NO: 7 (chromosome 6 haplotype Medium), or is homozygous for SEQ ID NO: 5 and SEQ ID NO: 6 (chromosome 6 haplotype Medium), or is homozygous for SEQ ID NO: 5 and SEQ ID NO: (chromosome 6 haplotype Large);
wherein the wild type, functional Ts-protein is encoded by a gene named Ts-gene, said Ts-gene encodes wild type, functional Ts-protein of SEQ ID NO: 1 or a protein comprising at least 90%, 91%, 92%, 93%, 94%, 95%, 96%, 97%, 98% or 99% sequence identity to SEQ ID NO: 1.

Steps i) above relates to the selection of a plant that combines the genetics which result in the absence of a functional Ts-protein on chromosome 2 (haplotype 'NO') with either the 'S' (Small), 'M' (Medium) or 'L' (Large) haplotype for chromosome 6 in the genome, whereby such a plant is predicted to produce an average seed size of 0.07 g/10 seeds to 0.26 g/10 seeds in its fruits.

The chromosome 2 haplotype 'NO' can genetically be due to a deletion of all or part of the Ts-gene, so that no functional Ts-protein is being made. For example, one or more regulatory elements of the Ts-gene may be deleted (or part thereof may be deleted) or part of the coding sequence may be deleted, or even the entire gene may be deleted, as found in plants comprising the deletion of SEQ ID NO: 8. In one aspect, plants comprising the deletion of SEQ ID NO: 8 are selected for in the methods described herein. In another aspect, plants comprising a smaller deletion than the deletion of SEQ ID NO: 8 are selected, whereby all or part of the Ts-gene is deleted. Alternatively, the chromosome 2 haplotype 'NO' can genetically be due to the presence of a mutant allele of the Ts-gene, said mutant allele results in no expression of the Ts-gene or the mutant allele encodes a Ts-protein having loss-of-function compared to the wild type Ts-protein. See also Table 1 and elsewhere herein. For example a mutant ts-allele may comprise an insertion, replacement and/or deletion of one or more nucleotides compared to the wild type allele, whereby the allele becomes a knock-out allele or encodes a loss-of-function protein.

Steps ii) in the method above relates to the selection of a plant that combines the genetics which result in the reduced function of the Ts-protein on chromosome 2 (haplotype 'RE') with either the 'S' (Small), 'M' (Medium) or 'L' (Large) haplotype for chromosome 6 in the genome, whereby such a plant is predicted to produce an average seed size of 0.15 g/10 seeds to 0.61 g/10 seeds in its fruits.

The chromosome 2 haplotype 'RE' can genetically be due to a reduced expression of the Ts-gene encoding the wild type Ts-protein, resulting in lower amounts of Ts-protein being made in the plant homozygous for the mutant ts-allele, which may e.g., be due to mutations in one or more regulatory elements of the Ts-gene (for example in the promoter), or it can be genetically due to a mutant ts-allele being present, which produces a mutant Ts-protein that has reduced in vivo activity compared to the wild type Ts-protein. See also Table 1 and elsewhere herein. Thus, in one aspect, the plant comprises a mutant allele of the Ts gene, said mutant allele results in reduced expression of the Ts-gene or the mutant allele encodes a Ts-protein having reduced function compared to the wild type Ts-protein. Such a reduced function Ts-protein may, for example, comprise one or more amino acids inserted, deleted or replaced compared to the wild type, functional Ts-protein. One example of such a mutant ts-allele is the allele which encodes a mutant Ts-protein, wherein the Aspartic acid (D) at amino acid 204 of SEQ ID NO: 1 (or the equivalent amino acid of a functional variant which comprising at least 90% identity to SEQ ID NO: 1) is deleted or is replaced by a different amino acid, preferably by a Tyrosine (Y) or by another disfavored replacement of Aspartic Acid (D). In one aspect, plants comprising this mutant allele are selected for in the methods described herein. Other mutant alleles are described elsewhere herein and can be used in the method. It is preferred that there is some functional Ts-protein being made, but a reduced amount compared to the plant homozygous for the wild type allele, or that a reduced function Ts-protein is being made in equivalent amounts as compared to the plant homozygous for the wild type allele. So, for example the mutant allele is modified in the promoter so that gene expression is equal to or less than 90%, 80%, 70%, 60%, 50%, 40%, 30%, 20% or 10% of the wild type level of gene expression, or the mutant allele encodes a mutant protein which has reduced function. For example the mutant Ts-protein may have a wild type/functional Acetyl transferase domain (e.g. the same as in the wild type protein, from amino acid 54 to 146 of SEQ ID NO: 1), but the mutant protein may have a reduced activity due to one or more amino acids being inserted, deleted or replaced outside of the Acetyl transferase domain, e.g. any amino acid in the region starting at amino acid 147 and ending at amino acid 412 or starting at amino acid 147 and ending at amino acid 400, or starting at amino acid 150 and ending at amino acid 390, especially in the region starting at amino acid 155 and ending at amino acid 265. Replacement one or more (e.g. 2, 3, 4, 5) amino acids in the middle region (which is from amino acid 155 to 265 of SEQ ID NO: 1 or the equivalent region in a sequence comprising at least 90% sequence identity to SEQ ID NO: 1) is likely to reduce protein function without abolishing the function altogether. Steps iii) in the method above relates to the selection of a plant that combines the genetics which result in a wild type, functional Ts-protein on chromosome 2 (haplotype 'WT') with either the 'S' (Small), 'M' (Medium) or 'L'(Large) haplotype for chromosome 6 in the genome, whereby such a plant is predicted to produce an average seed size of 0.27 g/10 seeds to 0.97 g/10 seeds in its fruits. The plant may, for example, comprise a Ts-allele which encodes the wild type, functional Ts-protein of SEQ ID NO: 1 or a protein (functional variant) comprising at least 90%, 91%, 92%, 93%, 94%, 95%, 96%, 97%, 98% or 99% sequence identity to SEQ ID NO: 1.

In the above method, the plant or plants selected are preferably inbred lines, which are homozygous for the chromosome 2 and chromosome 6 haplotypes. The selection of a plant line based on the chromosome 2 and chromosome 6 haplotype can occur based on information stored in a database. The skilled person can, for example, genotype all inbred lines for the chromosome 2 and chromosome 6 haplotypes, or analyze whole genome sequence information for the chromosome 2 and chromosome 6 haplotypes, and then base the selection of inbred lines on this information. One can thereby not only select inbred lines, but also parent lines to be used to produce F1 hybrids. The selection of suitable inbred parent lines to be crossed to produce F1 hybrid seeds, whereby the plants grown therefrom produce fruits having a predicted seed size, e.g. as shown in FIG. 3, can thus take place on a computer. The database and computer implemented method of selecting lines is also an aspect of the disclosure.

Also encompassed herein is, therefore, a method for producing F1 hybrid watermelon seeds (whereby e.g. the plants grown from the F1 hybrid seeds produce in their fruits a predicted seed size according to the model of FIG. 3), plants and plant parts comprising selecting a first parent line according to the method described above, having genotype i), ii) or iii) and selecting a second parent line according to the method described above, having genotype i), ii) or iii) and optionally further crossing said first parent line with said second parent line to produce F1 hybrid seeds. In the model of FIG. 3, it does not matter which of the parents (P1 or P2) is used as the male or female parent for the cross.

As it is desirable to produce F1 hybrids which produce medium seeds or small seeds, in a preferred aspect, both parent lines are selected as having a haplotype of i) or ii) to produce F1 hybrids which produce fruits upon pollination having predicted seed sizes of between 0.07 g/10 seeds and 0.61 g/10 seeds, as shown in FIG. 3. One can also select two parent lines which have the same haplotype for chromosome 2 and 6, and use these to make F1 hybrids. For example, both parent P1 and P2 may have chromosome 2 haplotype 'NO' and chromosome 6 haplotype "S", to produce F1 hybrids, the fruits of which have a predicted seed size 0f 0.07 g/10 seeds (see FIG. 3).

The F1 hybrid seeds made by the above method are also encompassed herein.

In a further aspect, a method for selecting a watermelon seed, plant or plant part is provided comprising:
  i) analyzing whether the seed, plant or plant part comprises one of the following haplotypes for a gene named Ts-gene, said Ts-gene encodes wild type, functional Ts-protein of SEQ ID NO: 1 or a protein comprising at least 90%, 91%, 92%, 93%, 94%, 95%, 96%, 97%, 98% or 99% sequence identity to SEQ ID NO: 1:
    a) a deletion of all or part of the Ts-gene, or a mutant allele of the Ts-gene, said mutant allele results in no expression of the Ts-gene or the mutant allele encodes a Ts-protein having loss-of-function compared to the wild type Ts-protein (chromosome 2 haplotype 'NO'),
    b) a mutant allele of the Ts-gene, which mutant allele encodes a mutant Ts-protein comprising one or more amino acids inserted, deleted or replaced compared to the wild type Ts-protein, said mutant Ts-protein having reduced function compared to the wild type Ts-protein (chromosome 2 haplotype 'RE');
    c) a wild type allele of the Ts-gene, encoding a functional Ts-protein (chromosome 2 haplotype 'WT'); and optionally
  ii) analyzing which haplotype for SNP 01 and INDEL 02 selected is present in the seed, plant or plant part selected from the combination of SEQ ID NO: 4 and SEQ ID NO: 6 (S), the combination of SEQ ID NO: 4 and SEQ ID NO: 7 (M), the combination of SEQ ID NO: 5 and SEQ ID NO: 6 (M) or the combination of SEQ ID NO: 5 and SEQ ID NO: 7 (L); and optionally
  iii) selecting a seed, plant or plant part comprising the desired combination of i) and ii).

As mentioned, the watermelon seed, plant or plant part selected is preferably an inbred watermelon plant, plant part or seed, which is homozygous for the selected haplotypes.

Furthermore, a method for selecting one or two watermelon lines to be used as parent lines for F1 hybrid seed production is provided, comprising selecting a first parent line and optionally a second parent line for
  i) comprising a haplotype for a gene named Ts-gene, said Ts-gene encodes wild type, functional Ts-protein of SEQ ID NO: 1 or a protein comprising at least 90%, 91%, 92%, 93%, 94%, 95%, 96%, 97%, 98% or 99% sequence identity to SEQ ID NO: 1, selected from:
- a) a deletion of all or part of the Ts-gene, or a mutant allele of the Ts-gene, said mutant allele results in no expression of the Ts-gene or the mutant allele encodes a Ts-protein having loss-of-function compared to the wild type Ts-protein (chromosome 2 haplotype 'NO');
- b) a mutant allele of the Ts-gene, which mutant allele encodes a mutant Ts-protein comprising one or more amino acids inserted, deleted or replaced compared to the wild type Ts-protein, said mutant Ts-protein having reduced function compared to the wild type Ts-protein (chromosome 2 haplotype 'RE'); or
- c) a wild type allele of the Ts-gene, encoding a functional Ts-protein (chromosome 2 haplotype 'WT'); and optionally ii) comprising a haplotype for SNP_01 and INDEL_02 selected from the combination of SEQ ID NO: 4 and SEQ ID NO: 6 (S), the combination of SEQ ID NO: 4 and SEQ ID NO: 7 (M), the combination of SEQ ID NO: 5 and SEQ ID NO: 6 (M) or the combination of SEQ ID NO: 5 and SEQ ID NO: 5 (L); and optionally iii) crossing the first parent line and the second parent line to produce F1 hybrid seeds.

Also provided is a method of crossing two watermelon parent lines to produce F1 hybrid seed, comprising:
crossing a first parent line being homozygous for a haplotype for a gene named Ts-gene selected from:
- a) a deletion of all or part of the Ts-gene, or a mutant allele of the Ts-gene, said mutant allele results in no expression of the Ts-gene or the mutant allele encodes a Ts-protein having loss-of-function compared to the wild type Ts-protein (chromosome 2 haplotype 'NO');
- b) a mutant allele of the Ts-gene, which mutant allele encodes a mutant Ts-protein comprising one or more amino acids inserted, deleted or replaced compared to the wild type Ts-protein, said mutant Ts-protein having reduced function compared to the wild type Ts-protein (chromosome 2 haplotype 'RE'); or
- c) a wild type allele of the Ts-gene, encoding a functional Ts-protein (chromosome 2 haplotype 'WT'); and optionally being homozygous for a haplotype for SNP_01 and INDEL_02 selected from i) the combination of SEQ ID NO: 4 and SEQ ID NO: 6 (S), or ii) the combination of SEQ ID NO: 4 and SEQ ID NO: 7 or the combination of SEQ ID NO: 5 and SEQ ID NO: 6 (M) or iii) the combination of SEQ ID NO: 5 and SEQ ID NO: 7 (L);

with a second parent line being homozygous for a haplotype for the Ts-gene selected from:
- a) a deletion of all or part of the Ts-gene, or a mutant allele of the Ts-gene, said mutant allele results in no expression of the Ts-gene or the mutant allele encodes a Ts-protein having loss-of-function compared to the wild type Ts-protein (chromosome 2 haplotype 'NO');
- b) a mutant allele of the Ts-gene, which mutant allele encodes a mutant Ts-protein comprising one or more amino acids inserted, deleted or replaced compared to the wild type Ts-protein, said mutant Ts-protein having reduced function compared to the wild type Ts-protein (chromosome 2 haplotype 'RE'); or
- c) a wild type allele of the Ts-gene, encoding a functional Ts-protein (chromosome 2 haplotype 'WT'); and optionally being homozygous for a haplotype for SNP_01 and INDEL_02 selected from i) the combination of SEQ ID NO: 4 and SEQ ID NO: 6 (S), or ii) the combination of SEQ ID NO: 4 and SEQ ID NO: 7 or the combination of SEQ ID NO: 5 and SEQ ID NO: 6 (M) or iii) the combination of SEQ ID NO: 5 and SEQ ID NO: 7 (L);

and obtaining the F1 hybrid seeds, optionally cleaning, drying and packaging the F1 hybrid seeds, wherein said Ts-gene is the gene which encodes a wild type, functional Ts-protein of SEQ ID NO: 1 or a protein comprising at least 90%, 91%, 92%, 93%, 94%, 95%, 96%, 97%, 98% or 99% sequence identity to SEQ ID NO: 1.

The watermelon plants used herein are preferably diploid, cultivated watermelons, which produce seeded fruits upon self-pollination. Triploid watermelons produce seedless fruits.

As mentioned, the haplotype or genotype selection of the lines or plants can take place on a computer, provided that molecular methods have been used to determine the haplotype or genotype of the lines or plants, such as sequencing, genotyping methods (e.g. SNP genotyping assays, such as KASP assays, etc.), PCR based methods, hybridization based methods, etc., as known in the art. If the data is stored in a database, selection according to the model of FIG. 2 or 3 can take place from the database.

EXAMPLES

Example 1—QTL Mapping of Seed Weight

In order to map QTLs for seed weight, mapping populations were generated as follows: To generate these mapping populations, two parents of different seed sizes were crossed to produce F1. The F1 were then selfed to produce F2 seed. Genome-wide markers were run on DNA samples from F2 lines and the seed produced from the F2 lines were then phenotyped. The genotypic and phenotypic data were used to map the QTL to loci on chromosomes 2 and/or 6. There were fifteen F2 populations that were used for QTL mapping (different years and locations), which were needed to capture all the combinations of the interactions of the alleles at chromosome 2 and 6 to build the model.

The populations were phenotyped for average seed weight (g/10 seeds) by either measuring seed dimensions (width and length) and/or by weighing 10 seed from each line (at least three measurements from a seedlot, wherein the seedlot comprises the seeds of at least three fruits).

Two QTLs were identified, one on chromosome 2 and one on chromosome 6, which together determine the final seed size of the seeds produced in the fruits, as further described in Example 3.

The QTL on chromosome 2 was fine mapped to the Ts-gene, as described in Example 2.

For the QTL on chromosome 6, two markers closely linked to the QTL were found. It was found that the haplotype for these two markers (shown in Table 3), in combination with the haplotype on chromosome 2 can be used to predict seed size and to select parent lines, which when crossed, will result in F1 hybrids with a predicted seed size in their fruits, as further shown in Example 3.

TABLE 3

| Marker name | Marker sequence |
|---|---|
| SNP_01 marker comprising G at nucleotide 61 | TAGATAACTCTTTGATAATCAAATCCTAAATCCCTTAGTTATTAGGGATCATACAAATTTG TTAATCCACATTTACCAGTTACTAAAAGGCAGCATTATTAAAAAAAGAAAAATCCCAATA (SEQ ID NO: 4) |
| SNP_01 marker comprising T at nucleotide 61 | TAGATAACTCTTTGATAATCAAATCCTAAATCCCTTAGTTATTAGGGATCATACAAATTTT TTAATCCACATTTACCAGTTACTAAAAGGCAGCATTATTAAAAAAAGAAAAATCCCAATA (SEQ ID NO: 5) |
| INDEL_02 marker comprising a deletion | atgtaacata tttagtccat tcaactatta agtgcgttac tacctcgact aaaaaattta gtacattcaa cgctcacgta ctttaaaatg tttaaattta gttattacac gttcaataaa tcttaaaact taaaattgct c (SEQ ID NO: 6) |
| INDEL_02 marker lacking the deletion/ comprising an insertion | atgtaacata tttagtccat tcaactatta agtgcgttac tacctcgact aaaaaattta gtacattcaa ctagcaagag cgttactact tcaactaaaa atatccattt cattttagct cacgtacttt aaaatgttta aatttagtta ttacacgttc aataaatctt aaaacttaaa attgctc (SEQ ID NO: 7) |

Example 2—Identification of the Ts-Gene

The is-gene mutation as originally found in the Sugar Baby is mutant plant was mapped by making five F2 populations, all sharing same male as an inbred line containing the is-gene mutant with an average seed size <=0.07 gr/10 seeds, and as female, 5 different inbred lines with an average seed size between 0.12 and 0.46 gr/10 seeds. As a result of the QTL mapping, the is-gene mutant was found to be located on chromosome 2 of the watermelon genome.

It was found that the is-gene mutant plant contained a large deletion in chromosome 2 in homozygous form and that this deletion caused the reduction in seed length when the deletion was present in homozygous form (i.e., deletion on both chromosomes). The sequence deleted is shown in SEQ ID NO: 8.

As shown in Table 4, the plants homozygous for the deletion of SEQ ID NO: 8, had the average seed weight (expressed in g/10 seeds) reduced and the average seed length reduced compared to plants lacking the deletion of SEQ ID NO: 8.

TABLE 4

| | Average Seed length | g/10 seeds | Presence of deletion of SEQ ID NO: 8 |
|---|---|---|---|
| WH9716 | 5.25 mm | 0.13 g | Homozygous |
| Female parent of WH9716 | | 0.12 | Homozygous |
| male parent of WH9716 | | 0.11 | Homozygous |
| Sugar Baby ts mutant plant | 4.2 mm* | 0.06 g | Homozygous |
| Sidekick | 10 mm | 0.57 g | Not deleted |

*according to Zhang 1996, Cucurbit Genetics Cooperative Report 19: 67-69

To measure gram per 10 seeds (g/10 seeds), three measurements of a seedlot per genotype were done and the average of the three measurements is indicated.

A BLAST was carried out on the website cucurbitgenomics.org using SEQ ID NO: 8.

SEQ ID NO: 8 is present on the watermelon 97103v1 genome on chromosome 2 starting at nucleotide 29916076 and ending at nucleotide 29902113. Likewise, the reverse complement of SEQ ID NO: 8 is present on the watermelon 97103v1 genome starting at nucleotide 29902113 and ending at nucleotide 29916076.

Upon further analysis of the deleted sequence on chromosome 2, two genes were found to be in the deleted region, as well as several ESTs (Expressed Sequence Tags). Cla013377 was on the minus strand of the watermelon 97103 v1 genome and Cla013376 was on the plus strand. Cla013376 was indicated to encode a BCL-2 'binding anthanogene-1' protein, indicated as being an apoptosis regulator protein. Cla013377 on the other hand (located on the minus strand from nucleotide 29904246 to 29906227) encoded an Acetyltransferase GNAT family protein. It was therefore hypothesized, based on the putative function of these proteins, that the deletion of Cla013377 is causal for the reduced seed length and reduced seed weight of seeds produced in fruits of plants homozygous for the deletion of SEQ ID NO: 8. This was later confirmed, as shown in the further examples.

Cla013377 was thus the wild type Ts gene, which when deleted resulted in a reduction in seed weight and length. It encodes the wild type, functional protein of SEQ ID NO: 1. In the genome of Charleston Grey, the encoded wild type Ts-protein was indicated to contain several additional amino acids at the C-terminal end, which is however due to an error in annotation of introns and exons. The genomic sequences are identical and both encode the protein of SEQ ID NO: 1. The wild type Ts-gene is called C1CG02G019400 in the Charleston Grey genome and Cla013377 in the 97103 v1 genome.

To confirm this hypothesis, various watermelon lines were screened for the Ts gene. Interestingly, one variety was found, SP-4, which contained a Ts protein wherein a single amino acid was changed, compared to the wild type protein. The D (Asp) at position 204 of SEQ ID NO: 1 was changed to Y (Tyr), see FIG. 1. Using Provean analysis, the single amino acid change D204Y is predicted as being "deleterious", i.e., reducing protein function. This is supported by the further examples.

Example 3—Development of Seed Size (SSZ) Selection and Breeding Methods

About 200 watermelon inbred lines were genotyped for the chromosome 2 and chromosome 6 haplotypes and were phenotyped for average seed size (g/10 seeds) in their fruits.

For phenotyping 3-5 plants per inbred lines were grown in the field in a completely randomized design. Average seed size was measured by three times weighing 10 seed of bulk seeds harvested from at least 3 fruits to get an average of three measurements.

Genotyping was done in the following way for the chromosome 2 locus and for the two chromosome 6 loci.

For the chromosome 2 locus, the three haplotypes 'NO', 'RE' and 'WT' were distinguished in the following way

| Chromosome 2 haplotype | | In the results below this is indicated as |
|---|---|---|
| 'NO'—no functional Ts protein | SEQ ID NO: 8 is absent | D (Deletion) |
| 'RE'—Ts protein has reduced function | The Ts protein is a mutant protein, comprising Y at amino acid 204 of SEQ ID NO: 1 | A Adenine nucleotide (ATG codon on the minus strand; TAC codon on the plus strand; encoding amino acid Y) |
| 'WT'—wild type Ts protein is present | The Ts protein is the wild type protein, comprising D at amino acid 204 of SEQ ID NO: 1 | C (Cytosine) nucleotide (CTG codon on the minus strand or a GAC codon on the plus strand; encoding amino acid D) |

For the two chromosome 6 loci, SNP analysis for the SNP 01 marker (nucleotide G or T) was done and an analysis of the genotype for INDEL 02 marker (indicated as D for deletion, or I for insertion). Lines were genotyped with four KASP assays designed to differentiate the three alleles at the locus on chromosome 2 and 6.

Figure 4:
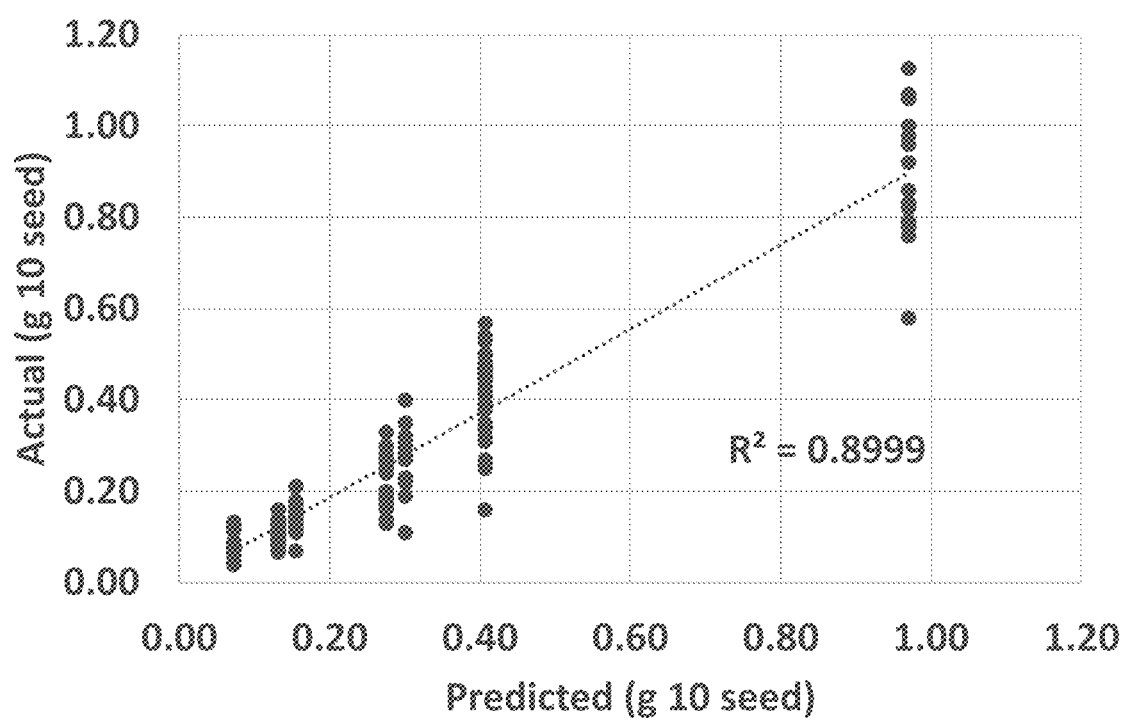
FIG. 4 shows a correlation of actual average seeds size (SSZ, g/10 seeds, average of three independent measurements of a seedlot per line) of inbred lines with predicted average seed size for inbred lines as shown in FIG. 2.

In addition, a model was developed (shown in FIG. 2) to predict seed size based on the chromosome 2 and chromosome 6 haplotypes. Regression analysis was done for determining whether actual and predicted seed sizes correlate. The result is shown in FIG. 4. A regression line was determined by the method of ordinary least squares to define a line that most closely fit the data. An R squared value ($R^2$) was calculated to show the variance explained by the predictions.

Genotyping and Phenotyping Results for Inbred Lines (Homozygous)

| Chr_02 | Chr 6 SNP_01 | Chr 6 SNP_02 | Index | Predicted SSZ (g per 10 seed) | Actual SSZ (g per 10 seed) | Deviation from actual (g per 10 seed) |
|---|---|---|---|---|---|---|
| DD | GG | DD | 1 | 0.07 | 0.04 | 0.03 |
| DD | GG | DD | 1 | 0.07 | 0.04 | 0.03 |
| DD | GG | DD | 1 | 0.07 | 0.05 | 0.03 |
| DD | GG | DD | 1 | 0.07 | 0.06 | 0.01 |
| DD | GG | II | 2 | 0.13 | 0.07 | 0.06 |
| DD | GG | DD | 1 | 0.07 | 0.07 | 0.00 |
| DD | GG | DD | 1 | 0.07 | 0.07 | 0.00 |
| DD | GG | DD | 1 | 0.07 | 0.07 | 0.00 |
| DD | GG | II | 2 | 0.13 | 0.07 | 0.06 |
| DD | GG | DD | 1 | 0.07 | 0.08 | 0.00 |
| DD | GG | DD | 1 | 0.07 | 0.08 | 0.01 |
| DD | GG | II | 2 | 0.13 | 0.08 | 0.05 |
| DD | GG | DD | 1 | 0.07 | 0.08 | 0.01 |
| DD | GG | II | 2 | 0.13 | 0.09 | 0.05 |
| DD | GG | II | 2 | 0.13 | 0.09 | 0.05 |
| DD | GG | DD | 1 | 0.07 | 0.09 | 0.02 |
| DD | GG | II | 2 | 0.13 | 0.09 | 0.04 |
| DD | GG | II | 2 | 0.13 | 0.09 | 0.04 |
| DD | GG | II | 2 | 0.13 | 0.09 | 0.04 |
| DD | GG | II | 2 | 0.13 | 0.09 | 0.04 |
| DD | GG | II | 2 | 0.13 | 0.09 | 0.04 |
| DD | GG | II | 2 | 0.13 | 0.10 | 0.04 |
| DD | GG | II | 2 | 0.13 | 0.1 | 0.03 |
| DD | GG | II | 2 | 0.13 | 0.1 | 0.03 |
| DD | GG | II | 2 | 0.13 | 0.1 | 0.03 |
| DD | GG | II | 2 | 0.13 | 0.11 | 0.02 |
| DD | GG | II | 2 | 0.13 | 0.11 | 0.02 |
| DD | GG | II | 2 | 0.13 | 0.11 | 0.02 |
| DD | GG | II | 2 | 0.13 | 0.11 | 0.02 |
| DD | GG | II | 2 | 0.13 | 0.11 | 0.02 |
| DD | GG | DD | 1 | 0.07 | 0.12 | 0.04 |
| DD | GG | DD | 1 | 0.07 | 0.12 | 0.04 |
| DD | GG | II | 2 | 0.13 | 0.12 | 0.01 |
| DD | GG | DD | 1 | 0.07 | 0.12 | 0.05 |
| DD | GG | DD | 1 | 0.07 | 0.12 | 0.05 |
| DD | GG | II | 2 | 0.13 | 0.13 | 0.01 |
| DD | GG | DD | 1 | 0.07 | 0.13 | 0.05 |
| DD | GG | DD | 1 | 0.07 | 0.13 | 0.06 |
| DD | GG | II | 2 | 0.13 | 0.13 | 0.00 |
| DD | GG | DD | 1 | 0.07 | 0.13 | 0.06 |
| DD | GG | II | 2 | 0.13 | 0.13 | 0.00 |
| DD | GG | II | 2 | 0.13 | 0.13 | 0.00 |
| DD | GG | II | 2 | 0.13 | 0.13 | 0.00 |
| DD | GG | II | 2 | 0.13 | 0.13 | 0.00 |
| DD | GG | DD | 1 | 0.07 | 0.13 | 0.06 |
| DD | GG | II | 2 | 0.13 | 0.13 | 0.00 |
| DD | GG | II | 2 | 0.13 | 0.14 | 0.01 |
| DD | GG | II | 2 | 0.13 | 0.14 | 0.01 |
| DD | GG | II | 2 | 0.13 | 0.14 | 0.01 |
| DD | GG | II | 2 | 0.13 | 0.16 | 0.03 |
| DD | GG | II | 2 | 0.13 | 0.16 | 0.03 |
| AA | GG | DD | 4 | 0.15 | 0.07 | 0.08 |
| AA | GG | DD | 4 | 0.15 | 0.11 | 0.04 |
| AA | GG | II | 5 | 0.30 | 0.11 | 0.19 |
| AA | GG | DD | 4 | 0.15 | 0.12 | 0.04 |
| AA | GG | DD | 4 | 0.15 | 0.13 | 0.03 |
| AA | GG | DD | 4 | 0.15 | 0.13 | 0.02 |
| AA | GG | DD | 4 | 0.15 | 0.13 | 0.02 |
| AA | GG | DD | 4 | 0.15 | 0.13 | 0.02 |
| AA | GG | DD | 4 | 0.15 | 0.13 | 0.02 |
| AA | GG | DD | 4 | 0.15 | 0.14 | 0.02 |
| AA | GG | DD | 4 | 0.15 | 0.14 | 0.02 |
| AA | GG | DD | 4 | 0.15 | 0.14 | 0.02 |
| AA | GG | DD | 4 | 0.15 | 0.14 | 0.01 |
| AA | GG | DD | 4 | 0.15 | 0.14 | 0.01 |
| AA | GG | DD | 4 | 0.15 | 0.14 | 0.01 |
| AA | GG | DD | 4 | 0.15 | 0.14 | 0.01 |
| AA | GG | DD | 4 | 0.15 | 0.15 | 0.01 |
| AA | GG | DD | 4 | 0.15 | 0.15 | 0.01 |
| AA | GG | DD | 4 | 0.15 | 0.15 | 0.01 |
| AA | GG | DD | 4 | 0.15 | 0.15 | 0.01 |
| AA | GG | DD | 4 | 0.15 | 0.15 | 0.01 |
| AA | GG | DD | 4 | 0.15 | 0.15 | 0.00 |
| AA | GG | DD | 4 | 0.15 | 0.15 | 0.00 |
| AA | GG | DD | 4 | 0.15 | 0.15 | 0.00 |
| AA | GG | DD | 4 | 0.15 | 0.16 | 0.00 |
| AA | GG | DD | 4 | 0.15 | 0.16 | 0.00 |
| AA | GG | DD | 4 | 0.15 | 0.16 | 0.00 |
| AA | GG | DD | 4 | 0.15 | 0.16 | 0.00 |
| AA | GG | DD | 4 | 0.15 | 0.16 | 0.00 |
| AA | GG | DD | 4 | 0.15 | 0.17 | 0.02 |
| AA | GG | DD | 4 | 0.15 | 0.17 | 0.02 |
| AA | GG | DD | 4 | 0.15 | 0.18 | 0.02 |
| AA | GG | DD | 4 | 0.15 | 0.18 | 0.02 |
| AA | GG | DD | 4 | 0.15 | 0.18 | 0.03 |

| Chr_02 | Chr 6 SNP_01 | Chr 6 SNP_02 | Index | Predicted SSZ (g per 10 seed) | Actual SSZ (g per 10 seed) | Deviation from actual (g per 10 seed) |
|---|---|---|---|---|---|---|
| AA | GG | II | 5 | 0.30 | 0.19 | 0.11 |
| AA | GG | DD | 4 | 0.15 | 0.21 | 0.06 |
| AA | GG | DD | 4 | 0.15 | 0.21 | 0.06 |
| AA | GG | II | 5 | 0.30 | 0.22 | 0.08 |
| AA | GG | II | 5 | 0.30 | 0.23 | 0.07 |
| AA | GG | II | 5 | 0.30 | 0.23 | 0.07 |
| AA | GG | II | 5 | 0.30 | 0.27 | 0.03 |
| AA | GG | II | 5 | 0.30 | 0.28 | 0.02 |
| AA | GG | II | 5 | 0.30 | 0.28 | 0.02 |
| AA | GG | II | 5 | 0.30 | 0.30 | 0.00 |
| AA | GG | II | 5 | 0.30 | 0.31 | 0.01 |
| AA | GG | II | 5 | 0.30 | 0.32 | 0.02 |
| AA | GG | II | 5 | 0.30 | 0.35 | 0.05 |
| AA | GG | II | 5 | 0.30 | 0.4 | 0.10 |
| AA | GG | II | 5 | 0.30 | 0.4 | 0.10 |
| CC | GG | DD | 7 | 0.27 | 0.13 | 0.14 |
| CC | GG | DD | 7 | 0.27 | 0.13 | 0.14 |
| CC | GG | DD | 7 | 0.27 | 0.14 | 0.13 |
| CC | GG | DD | 7 | 0.27 | 0.16 | 0.11 |
| CC | GG | II | 8 | 0.41 | 0.16 | 0.25 |
| CC | GG | DD | 7 | 0.27 | 0.17 | 0.11 |
| CC | GG | DD | 7 | 0.27 | 0.17 | 0.10 |
| CC | GG | DD | 7 | 0.27 | 0.18 | 0.10 |
| CC | GG | DD | 7 | 0.27 | 0.18 | 0.09 |
| CC | GG | DD | 7 | 0.27 | 0.19 | 0.09 |
| CC | GG | DD | 7 | 0.27 | 0.19 | 0.08 |
| CC | GG | DD | 7 | 0.27 | 0.19 | 0.08 |
| CC | GG | DD | 7 | 0.27 | 0.19 | 0.08 |
| CC | GG | DD | 7 | 0.27 | 0.2 | 0.07 |
| CC | GG | DD | 7 | 0.27 | 0.2 | 0.07 |
| CC | GG | DD | 7 | 0.27 | 0.2 | 0.07 |
| CC | GG | DD | 7 | 0.27 | 0.2 | 0.07 |
| CC | GG | DD | 7 | 0.27 | 0.2 | 0.07 |
| CC | GG | DD | 7 | 0.27 | 0.2 | 0.07 |
| CC | GG | DD | 7 | 0.27 | 0.24 | 0.03 |
| CC | GG | DD | 7 | 0.27 | 0.25 | 0.02 |
| CC | GG | DD | 7 | 0.27 | 0.25 | 0.02 |
| CC | GG | DD | 7 | 0.27 | 0.25 | 0.02 |
| CC | GG | II | 8 | 0.41 | 0.25 | 0.16 |
| CC | GG | DD | 7 | 0.27 | 0.26 | 0.01 |
| CC | GG | II | 8 | 0.41 | 0.26 | 0.15 |
| CC | GG | II | 8 | 0.41 | 0.26 | 0.15 |
| CC | GG | DD | 7 | 0.27 | 0.27 | 0.01 |
| CC | GG | DD | 7 | 0.27 | 0.27 | 0.00 |
| CC | GG | II | 8 | 0.41 | 0.27 | 0.14 |
| CC | GG | DD | 7 | 0.27 | 0.28 | 0.01 |
| CC | GG | DD | 7 | 0.27 | 0.3 | 0.03 |
| CC | GG | DD | 7 | 0.27 | 0.3 | 0.03 |
| CC | GG | II | 8 | 0.41 | 0.31 | 0.10 |
| CC | GG | II | 8 | 0.41 | 0.32 | 0.09 |
| CC | GG | DD | 7 | 0.27 | 0.33 | 0.06 |
| CC | GG | II | 8 | 0.41 | 0.34 | 0.07 |
| CC | GG | II | 8 | 0.41 | 0.34 | 0.07 |
| CC | GG | II | 8 | 0.41 | 0.34 | 0.07 |
| CC | GG | II | 8 | 0.41 | 0.34 | 0.07 |
| CC | GG | II | 8 | 0.41 | 0.34 | 0.07 |
| CC | GG | II | 8 | 0.41 | 0.35 | 0.06 |
| CC | GG | II | 8 | 0.41 | 0.35 | 0.06 |
| CC | GG | II | 8 | 0.41 | 0.38 | 0.03 |
| CC | GG | II | 8 | 0.41 | 0.39 | 0.02 |
| CC | GG | II | 8 | 0.41 | 0.39 | 0.02 |
| CC | GG | II | 8 | 0.41 | 0.41 | 0.00 |
| CC | GG | II | 8 | 0.41 | 0.41 | 0.00 |
| CC | GG | II | 8 | 0.41 | 0.42 | 0.01 |
| CC | GG | II | 8 | 0.41 | 0.42 | 0.01 |
| CC | GG | II | 8 | 0.41 | 0.42 | 0.01 |
| CC | GG | II | 8 | 0.41 | 0.43 | 0.02 |
| CC | GG | II | 8 | 0.41 | 0.44 | 0.04 |
| CC | GG | II | 8 | 0.41 | 0.45 | 0.04 |
| CC | GG | II | 8 | 0.41 | 0.45 | 0.04 |
| CC | GG | II | 8 | 0.41 | 0.45 | 0.04 |
| CC | GG | II | 8 | 0.41 | 0.45 | 0.04 |
| CC | GG | II | 8 | 0.41 | 0.46 | 0.05 |
| CC | GG | II | 8 | 0.41 | 0.46 | 0.05 |
| CC | GG | II | 8 | 0.41 | 0.47 | 0.06 |
| CC | GG | II | 8 | 0.41 | 0.47 | 0.06 |
| CC | GG | II | 8 | 0.41 | 0.47 | 0.06 |
| CC | GG | II | 8 | 0.41 | 0.47 | 0.06 |
| CC | GG | II | 8 | 0.41 | 0.48 | 0.07 |
| CC | GG | II | 8 | 0.41 | 0.48 | 0.07 |
| CC | GG | II | 8 | 0.41 | 0.5 | 0.09 |
| CC | GG | II | 8 | 0.41 | 0.5 | 0.09 |
| CC | GG | II | 8 | 0.41 | 0.5 | 0.09 |
| CC | GG | II | 8 | 0.41 | 0.53 | 0.12 |
| CC | GG | II | 8 | 0.41 | 0.53 | 0.12 |
| CC | GG | II | 8 | 0.41 | 0.54 | 0.13 |
| CC | GG | II | 8 | 0.41 | 0.57 | 0.16 |
| CC | TT | II | 9 | 0.97 | 0.58 | 0.39 |
| CC | TT | II | 9 | 0.97 | 0.76 | 0.21 |
| CC | TT | II | 9 | 0.97 | 0.76 | 0.21 |
| CC | TT | II | 9 | 0.97 | 0.78 | 0.19 |
| CC | TT | II | 9 | 0.97 | 0.79 | 0.18 |
| CC | TT | II | 9 | 0.97 | 0.82 | 0.15 |
| CC | TT | II | 9 | 0.97 | 0.83 | 0.14 |
| CC | TT | II | 9 | 0.97 | 0.83 | 0.14 |
| CC | TT | II | 9 | 0.97 | 0.86 | 0.11 |
| CC | TT | II | 9 | 0.97 | 0.92 | 0.05 |
| CC | TT | II | 9 | 0.97 | 0.96 | 0.01 |
| CC | TT | II | 9 | 0.97 | 0.98 | 0.01 |
| CC | TT | II | 9 | 0.97 | 1 | 0.03 |
| CC | TT | II | 9 | 0.97 | 1.06 | 0.09 |
| CC | TT | II | 9 | 0.97 | 1.07 | 0.10 |
| CC | TT | II | 9 | 0.97 | 1.13 | 0.16 |
| DD | GG | DD | 1 | 0.07 | 0.04 | 0.03 |

The same genotyping and phenotyping as for the inbred parent lines was done for more than 200 F1 hybrids made from various combinations of inbred parent lines (data not shown).

Here a model was also developed (shown in FIG. 3) to predict seed size based on the chromosome 2 and chromosome 6 haplotypes.

Figure 5:
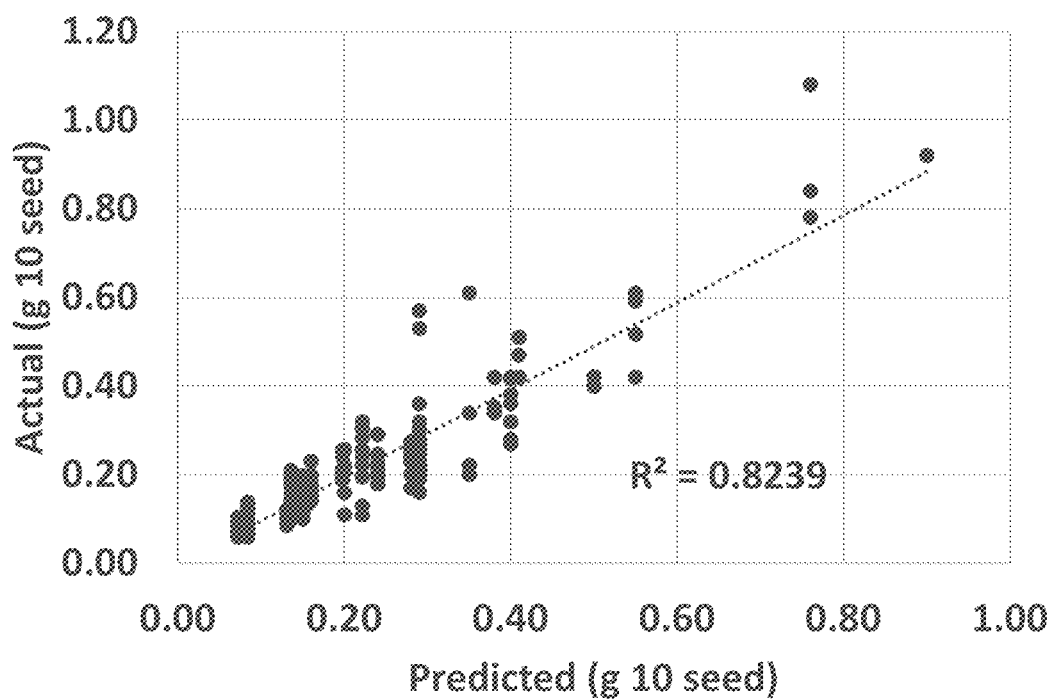
FIG. 5 shows a correlation of actual average seeds size (SSZ, g/10 seeds, average of three independent measurements of a seedlot per line) with predicted average seed size for fruits of F1 hybrid plants (F1 hybrid is P1 crossed with P2) as shown in FIG. 3.

Regression analysis was done for determining whether actual seed sizes measured in fruits of the F1 hybrid plants and the predicted seed sizes of the model correlate. A regression line was determined by the method of ordinary least squares to define a line that most closely fit the data. An R squared value ($R^2$) was calculated to show the variance explained by the predictions. The result is shown in FIG. 5.

The invention claimed is:

1. A method of producing F1 hybrid seed, comprising crossing a first parent line being homozygous for a haplotype for a gene named Ts-gene selected from:
   a) a deletion of all or part of the Ts-gene, or a mutant allele of the Ts-gene, said mutant allele results in no expression of the Ts-gene or the mutant allele encodes a Ts-protein having loss-of-function compared to the wild type Ts-protein (chromosome 2 haplotype 'NO');
   b) a mutant allele of the Ts-gene, which mutant allele encodes a mutant Ts-protein comprising one or more amino acids inserted, deleted or replaced compared to the wild type Ts-protein, said mutant Ts-protein having reduced function compared to the wild type Ts-protein (chromosome 2 haplotype 'RE'); or
   c) a wild type allele of the Ts-gene, encoding a functional Ts-protein (chromosome 2 haplotype 'WT');
   and
   being homozygous for a haplotype for SNP_01 and INDEL_02 selected from i) the combination of SEQ ID NO: 4 and SEQ ID NO: 6, or ii) the combination of SEQ ID NO: 4 and SEQ ID NO: 7 or the combination of SEQ ID NO: 5 and SEQ ID NO: 6 or iii) the combination of SEQ ID NO: 5 and SEQ ID NO: 7;

with a second parent line being homozygous for a haplotype for the Ts-gene selected from:
   a) a deletion of all or part of the Ts-gene, or a mutant allele of the Ts-gene, said mutant allele results in no expression of the Ts-gene or the mutant allele encodes a Ts-protein having loss-of-function compared to the wild type Ts-protein (chromosome 2 haplotype 'NO'),
   b) a mutant allele of the Ts-gene, which mutant allele encodes a mutant Ts-protein comprising one or more amino acids inserted, deleted or replaced compared to the wild type Ts-protein, said mutant Ts-protein having reduced function compared to the wild type Ts-protein (chromosome 2 haplotype 'RE'); or
   c) a wild type allele of the Ts-gene, encoding a functional Ts-protein (chromosome 2 haplotype 'WT');
   and
   being homozygous for a haplotype for SNP_01 and INDEL_02 selected from i) the combination of SEQ ID NO: 4 and SEQ ID NO: 6, or ii) the combination of SEQ ID NO: 4 and SEQ ID NO: 7 or the combination of SEQ ID NO: 5 and SEQ ID NO: 6 or iii) the combination of SEQ ID NO: 5 and SEQ ID NO: 7;

and obtaining the F1 hybrid seeds, optionally cleaning, drying and packaging the F1 hybrid seeds, wherein said Ts-gene is the gene which encodes a wild type, functional Ts-protein of SEQ ID NO: 1 or a protein comprising at least 95% sequence identity to SEQ ID NO: 1.

2. A watermelon plant or seed or plant part comprising at least one copy of a mutant allele of a gene named Ts-gene or comprises a deletion of all or part of the Ts-gene, said Ts-gene encodes a functional Ts-protein of SEQ ID NO: 1 or a protein comprising at least 95% sequence identity to SEQ ID NO: 1, wherein the mutant allele has reduced expression or no expression compared to the wild type allele of the Ts-gene, or wherein the mutant allele encodes a mutant Ts-protein having reduced function or loss of function compared to the wild type Ts-protein of SEQ ID NO: 1 or compared to a wild type Ts-protein comprising at least 95% sequence identity to SEQ ID NO: 1, wherein said deletion is not a deletion of SEQ ID NO: 8 but a different deletion of all or part of the Ts-gene and wherein said mutant allele does not encode a mutant Ts-protein in which the Aspartic acid (D) at amino acid 204 of SEQ ID NO: 1 is replaced by a Tyrosine (Y).

3. The watermelon plant or seed or plant part according to claim 2, wherein the mutant allele of the Ts-gene encodes a reduced function Ts-protein comprising one or more amino acids inserted, deleted or replaced compared to the wild type protein of SEQ ID NO: 1.

4. The watermelon plant or seed or plant part according to claim 2, wherein said plant or seed or plant part is homozygous for said mutant allele of the Ts-gene or for the deletion of all or part of the Ts-gene.

5. The watermelon, plant or seed or plant part according to claim 2, wherein the plant or seed is an inbred line or an F1 hybrid.

6. The method according to claim 1, wherein the selection of said first parent line and/or of said second parent line is made based on said genotype information of watermelon lines stored in a database.

7. The method according to claim 1, wherein the selection of inbred lines said first parent line and/or said second parent line is made based on information obtained by genotyping inbred lines for the chromosome 2 and chromosome 6 haplotypes, or by analyzing whole genome sequence information for the chromosome 2 and chromosome 6 haplotypes.

8. The method according to claim 7, wherein the selection of said first parent line and/or said second parent line comprises using molecular methods to determine the haplotype or genotype of inbred watermelon lines, and thereafter selecting said inbred watermelon line based on the haplotype or genotype determined by said molecular methods.

9. The method according to claim 8, wherein the molecular methods comprise sequencing, genotyping methods, PCR based methods or hybridization based methods.

* * * * *

SEQUENCE LISTING

<160> NUMBER OF SEQ ID NOS: 8

<210> SEQ ID NO 1
<211> LENGTH: 412
<212> TYPE: PRT
<213> ORGANISM: artificial

<220> FEATURE:
<223> OTHER INFORMATION: Wild type Ts protein of watermelon

<400> SEQUENCE: 1

```
Met Gly Phe Lys Gly Phe Val Ile Arg Ser Tyr Glu Glu Ser Gln Leu
1               5                   10                  15

Ser Asp Lys Ala Gln Val Met Asp Leu Glu Arg Arg Cys Glu Ile Gly
            20                  25                  30

Gln Ser Lys Arg Val Phe Leu Phe Thr Asp Thr Leu Gly Asp Pro Ile
        35                  40                  45

Cys Arg Ile Arg Asn Ser Pro Met Tyr Lys Met Leu Val Ala Glu Arg
    50                  55                  60

Asp Lys Glu Val Val Gly Val Ile Gln Gly Ser Ile Lys Pro Val Phe
65                  70                  75                  80

Phe Thr Ala His Lys Pro Pro Gly Leu Val Val Lys Leu Gly Tyr
                85                  90                  95

Ile Leu Gly Leu Arg Val Ala Pro Pro Tyr Arg Arg Arg Gly Ile Gly
                100                 105                 110

Ser Ser Leu Val Arg Arg Leu Glu Asp Trp Phe Leu Ser Asn Asp Val
            115                 120                 125

Asp Tyr Cys Cys Met Ala Thr Glu Lys Asp Asn His Ala Ser Leu Asn
130                 135                 140

Leu Phe Ile Asn Asn Leu Arg Tyr Ile Lys Phe Arg Thr Gly Arg Ile
145                 150                 155                 160

Leu Val Asn Pro Val Arg Asn His Pro Tyr Asn Met Asn Ser Ser Glu
                165                 170                 175

Ile Asn Ile Gln Lys Leu Lys Ile Glu Glu Ala Glu Ala Ile Tyr Lys
            180                 185                 190

Lys His Met Ala Ser Thr Glu Phe Phe Pro Lys Asp Ile Lys Asn Ile
        195                 200                 205

Leu Lys Asn Lys Leu Ser Leu Gly Thr Trp Val Ala Asn Phe Lys Gln
210                 215                 220

Pro Pro Trp Ser Ser Ser Asn Ser Val Gly Gly Asn Gly Gln Thr Met
225                 230                 235                 240

Ala Ser Ser Trp Ala Ile Val Ser Leu Trp Asn Ser Gly Glu Val Phe
                245                 250                 255

Lys Leu Arg Leu Gly Lys Ala Pro Phe Pro Trp Leu Ile Tyr Thr Lys
            260                 265                 270

Ser Leu Lys Ile Met Asp Lys Ile Phe Pro Cys Phe Lys Val Val Leu
        275                 280                 285

Val Pro Asn Phe Phe Lys Pro Phe Gly Phe Tyr Phe Val Tyr Gly Leu
290                 295                 300

His His Glu Gly Pro Phe Ser Glu Arg Leu Val Gly Ala Leu Cys Lys
305                 310                 315                 320

Phe Val His Asn Met Ala Leu Asn Asn Ser Lys Asp Asn Cys Lys Ala
                325                 330                 335

Ile Val Thr Glu Ile Gly Gly Asp Glu Asp Asp Gly Leu Lys Met Glu
            340                 345                 350

Ile Pro His Trp Lys Leu Leu Ser Cys Tyr Glu Asp Phe Trp Cys Ile
        355                 360                 365

Lys Ser Leu Lys Ser Lys Arg Tyr Asn Asn Ile Ser Asn Asp Asn Asp
        370                 375                 380

Asn Asp Asn Asp His Asp His His Ile Leu Glu Trp Thr Asn Ala Ser
385                 390                 395                 400
```

Pro Asn Arg Thr Leu Phe Val Asp Pro Arg Glu Val
            405                 410

<210> SEQ ID NO 2
<211> LENGTH: 1982
<212> TYPE: DNA
<213> ORGANISM: artificial
<220> FEATURE:
<223> OTHER INFORMATION: citrullus lanatus wild type genomic DNA
      encoding SEQ ID NO: 1

<400> SEQUENCE: 2

| | |
|---|---|
| atggggttta aaggctttgt tattcgaagc tacgaagaga gtcaattatc agataaagct | 60 |
| caagttatgg atcttgaacg aagatgtgaa attggccaat caaaacgtgt gtttctcttc | 120 |
| actgacactt tgggtgaccc catttgtagg atacgtaaca gtcccatgta aaaatgctg | 180 |
| gtaatctaat ttaattttaa ttaattgtgt tttttatag gttaattaat tattaatttg | 240 |
| tgaattgaaa attttttatt attaaggttg ctgagcggga caaggaagtg gttggtgtta | 300 |
| ttcaaggctc tataaaaccg gttttttta ctgctcataa accgccgccc ggtttggtgg | 360 |
| ttaaactggg ctacattctt ggcctgagag tggcaccgcc gtatcgccgc cgtggaattg | 420 |
| gctctagcct cgtccgccgt ttggaagatt ggttcctttc taatgatgtt gattactgtt | 480 |
| gtatggccac tgagaaagat aatcatgcct ctcttaatct cttcatcaat aatttgaggt | 540 |
| attttccatt tttttctttt tcttttaagt caacaattat gaattgggag agagcacgga | 600 |
| tcgaacaatc attttaaaa tggtaattag tgtcatttta tcttatgtgt tatactcaga | 660 |
| ttagctatta actctatctt ataatgtagg ttttgtcagt attttgagaa ctttcaaatt | 720 |
| tgtgtctaac tagtttttt ttccttagtt acttaccaaa cacgtgataa tattattata | 780 |
| tgatgaaatt tttatttt tttattttt tatttatttt ttattgtggc aagtaggagc | 840 |
| atcatactta ccaacaactt aatagatata aaattaaaaa tttaatggtc aaatcaaact | 900 |
| ttttcgagag taatttttaat gttgagtttt gcacttttaa atataattta cgtatgattt | 960 |
| tgaaggatta gattcatgtt tagtttgaag tggtttagaa tctggcaaaa gggattttaa | 1020 |
| caatttcaaa ctaacgcctc tcatatttgt agtttgggac gtcactttgc tattaattaa | 1080 |
| caaaatcaca tttttggaaa ttaacatatg attcacatgc aactcgtaaa tgaagttaaa | 1140 |
| cttgaaagtt tagaggcata ttagaaattt ctttaaatat tctttttccc aacaggtaca | 1200 |
| taaagtttag aacaggaagg atcttggtaa acccagtaag aaatcatcca tacaatatga | 1260 |
| attcatcaga aatcaacatt caaaagctaa aatagaagaa agcagaagca atatacaaaa | 1320 |
| aacacatggc ttcaacagag ttcttcccca agacataaa aaacatattg aaaaacaagt | 1380 |
| tgagtttagg gacatggtg gcaaatttca acaaccgcc atggtcgtcg tcgaactctg | 1440 |
| ttggaggaaa cgggcagact atggcgagta gctgggccat tgtaagtcta tggaacagtg | 1500 |
| gggaagtttt caagctaagg ctaggaaaag caccatttcc atggcttatc tacacaaaga | 1560 |
| gtttaaaaat tatggataaa attttcctt gctttaaagt ggttttggtg cctaattttt | 1620 |
| tcaagccatt tgggttctat tttgtttatg gattgcacca tgaaggcct ttttctgaga | 1680 |
| gattggttgg agctttgtgc aaatttgtgc acaatatggc attgaataat tcaaggata | 1740 |
| attgtaaagc tattgttact gagattggag gtgatgagga tgatgggctg aaaatggaga | 1800 |
| ttcctcattg gaaattgcta tcatgttatg aagattttg gtgcataaag tccttgaaaa | 1860 |
| gtaagagata taataatatt agtaatgata atgataacga taacgatcac gatcatcata | 1920 |

```
tattggaatg acaaatgcc tcacctaata gaactctctt tgtagaccca agagaggtat    1980
aa                                                                 1982
```

<210> SEQ ID NO 3
<211> LENGTH: 1239
<212> TYPE: DNA
<213> ORGANISM: artificial
<220> FEATURE:
<223> OTHER INFORMATION: cDNA encoding the wild type Ts-protein of SEQ
      ID NO: 1

<400> SEQUENCE: 3

```
atggggttta aaggctttgt tattcgaagc tacgaagaga gtcaattatc agataaagct     60
caagttatgg atcttgaacg aagatgtgaa attggccaat caaaacgtgt gtttctcttc    120
actgacactt tgggtgaccc catttgtagg atacgtaaca gtcccatgta taaaatgctg    180
gttgctgagc gggacaagga agtggttggt gttattcaag gctctataaa accggttttt    240
tttactgctc ataaaccgcc gcccggtttg gtggttaaac tgggctacat tcttggcctg    300
agagtggcac cgccgtatcg ccgccgtgga attggctcta gcctcgtccg ccgtttggaa    360
gattggttcc tttctaatga tgttgattac tgttgtatgg ccactgagaa agataatcat    420
gcctctctta atctcttcat caataatttg aggtacataa agtttagaac aggaaggatc    480
ttggtaaacc cagtaagaaa tcatccatac aaatatgaatt catcagaaat caacattcaa    540
aagctaaaaa tagaagaagc agaagcaata tacaaaaaac acatggcttc aacagagttc    600
ttccccaaag acataaaaaa catattgaaa aacaagttga gtttagggac atgggtggca    660
aatttcaaac aaccgccatg gtcgtcgtcg aactctgttg gaggaaacgg gcagactatg    720
gcgagtagct gggccattgt aagtctatgg aacagtgggg aagttttcaa gctaaggcta    780
ggaaaagcac catttccatg gcttatctac acaaagagtt aaaaattat ggataaaatt    840 tttccttgct ttaaagtggt tttggtgcct aattttttca gccatttgg gttctatttt    900 gtttatggat tgcaccatga aggcccttt tctgagagat tggttggagc tttgtgcaaa    960
tttgtgcaca atatggcatt gaataattca aaggataatt gtaaagctat tgttactgag   1020
attggaggtg atgaggatga tgggctgaaa atggagattc tcattggaa attgctatca   1080 tgttatgaag atttttggtg cataaagtcc ttgaaaagta agagatataa taatattagt   1140
aatgataatg taacgataa cgatcacgat catcatatat ggaatggac aaatgcctca   1200 cctaatagaa ctctctttgt agacccaaga gaggtataa                           1239
```

<210> SEQ ID NO 4
<211> LENGTH: 121
<212> TYPE: DNA
<213> ORGANISM: artificial
<220> FEATURE:
<223> OTHER INFORMATION: chromosome 6 SNP_01 marker comprising G at
      nucleotide 61

<400> SEQUENCE: 4

```
tagataactc tttgataatc aaatcctaaa tcccttagtt attagggatc atacaaattt     60
gttaatccac atttaccagt tactaaaagg cagcattatt aaaaaaagaa aaatcccaat    120
a                                                                    121
```

<210> SEQ ID NO 5
<211> LENGTH: 121
<212> TYPE: DNA
<213> ORGANISM: artificial

```
<220> FEATURE:
<223> OTHER INFORMATION: chromosome 6 SNP_01 marker comprising T at
      nucleotide 61

<400> SEQUENCE: 5
tagataactc tttgataatc aaatcctaaa tcccttagtt attagggatc atacaaattt    60
tttaatccac atttaccagt tactaaaagg cagcattatt aaaaaaagaa aaatcccaat   120
a                                                                  121

<210> SEQ ID NO 6
<211> LENGTH: 141
<212> TYPE: DNA
<213> ORGANISM: artificial
<220> FEATURE:
<223> OTHER INFORMATION: chromosome 6 INDEL marker comprising a deletion

<400> SEQUENCE: 6
atgtaacata tttagtccat tcaactatta agtgcgttac tacctcgact aaaaaattta    60
gtacattcaa cgctcacgta ctttaaaatg tttaaattta gttattacac gttcaataaa   120
tcttaaaact taaaattgct c                                            141

<210> SEQ ID NO 7
<211> LENGTH: 187
<212> TYPE: DNA
<213> ORGANISM: artificial
<220> FEATURE:
<223> OTHER INFORMATION: chromosome 6 INDEL marker not comprising a
      deletion

<400> SEQUENCE: 7
atgtaacata tttagtccat tcaactatta agtgcgttac tacctcgact aaaaaattta    60
gtacattcaa ctagcaagag cgttactact tcaactaaaa atatccattt cattttagct   120
cacgtacttt aaaatgttta aatttagtta ttacacgttc aataaatctt aaaacttaaa   180
attgctc                                                            187

<210> SEQ ID NO 8
<211> LENGTH: 13964
<212> TYPE: DNA
<213> ORGANISM: artificial
<220> FEATURE:
<223> OTHER INFORMATION: large genomic deletion on chromosome 2

<400> SEQUENCE: 8 ttttttttt ttttcgatt ttgaaaatga agtctataga cactacttcc atctcaaaat      60
ttattctttt gttatctaat ttttactaat gatttaaaaa accaagccaa aatttgaaaa   120
ctaaaaacag taacttttaa aaacttgttg tttttggaat ttgactaata aaaaatggga   180
aagaatattc tttattttca aaaacaaaat tattattaaa tatagcctaa atatttaaaa   240
aataataaat attagatact aaattattac tcgttgacaa tggttaaaaa aaaaaaaaaa   300
gcgaaagaat ttgataaaaa gagagagtaa taatattcca cttaacccaa catcacactg   360
cacagacatc ttattgggct tataacagag cccatttggg tccaatatca attgggaagc   420
ccacataaag caatatgtac agaaatgcca aaatagttta attcgattcg gttcggttct   480
aatgcaaaaa aatgggaaga aagagaatga actaatcaaa gagttcccaa tcatgagtta   540
tttttgtaga gctgatggtg agttttgaag ttggaggaat aaggctgcca aatccagatt   600
caaattcctc ccatttgcct cttttcattg ttgtttggtt taaaggattt gagattctaa   660
```

```
ccttcaactt gtcaattctg tccactaatt tctgtaccct aacaacctgt tttattccca    720
aaattataaa attacaattc taacgttatt caaattaatt gaaattgcgt aaaaacttat    780
caccaccaaa ataaacatag ttcaatgata attaacgtat actctttctc tcaatttccc    840
tactctacta tttgtacttc aaaaaaaaaa ttacatagtt caaaattaaa atttaattac    900
tatttttatc ttattttgt tcattgttaa ggggccaaaa tggagacttt ttaaaaccac     960
gggactaaaa ttgatatttt gaaagtaagt ggaccaaaat taactatagt taaaggttaa   1020
attgcaaatt tgtctcctat aatttagaaa aaattagaat ttggcccctg tagtttggag   1080
aaaattaaaa tctggtccat ttggttttaa aatctagaat tagttcctat ggtttgataa   1140
aaccttataa atgttcccta tagtttagtc tctacagtag tgagattatt tatgaggatt   1200
ttatcagatc atagagatta aattctaatt ataaactata ggattaaatt ttaactttct   1260
tcaaattata tggactaaat ttataattta accaaaatta aaggtcgtg aatctaaatg    1320 aaacaatgtg aaaaatataa aaactaaagt agtatttaaa cctaaaattt ttatctagtg   1380
ttcatgccac ctcagcattc ctatgatttc tatttatttt attcatgata dacgctaaat   1440
agaggtgtga ttaagacttt agggacatta atggaatttt cttctttaat caattattta   1500
tttattttga atagaatcct tcttgataag ttccttggttt cataatgtcc cacataaaaa   1560
tgtcatatca agggaaagaa ttaaaatcat tttgtcctat ttctgcaatt tttttagtct   1620
atatttatta attttttttt ttgagttaat aaataaatag ataaaatacc cattatcatt   1680
tttcacaatt tatattcatt gaattttcat acaatttagg agactttcat tattttaat    1740 tattttaagt ttgatggccc taggggagca ccagccacct aacccattaa tgattaaaact   1800 atcgtacttt ttattataaa taccaaaatt gaaaaattaa aatatatata tttaattta    1860 attcatattt tcaagtattc atttaataaa acttaaattt aatccatcat tattaaaatt   1920
gattaaataa tagtaaataa ttttctacca tagaaatata atatttaaat atataattca   1980
tccaaatgga atttagtgtt tttatttaa aaagttttg tcacaaaaat ttaaataaaa     2040
ataattttta aaaaaatatt tattttttaa gttaatccaa acttacataa aatccattct   2100
tttttttaga aaactataca aatctaataa ctaataataa taataaagat atatgttaat   2160
tattattgtt tgaaaagtta tatcatttaa tggatattaa atatgactaa tgcaaacata   2220
cccgacatta agagttaaca aaagagttt taaaagagaa attaggcggt aagtaaattt    2280
ataattcctc ttcataaagt tttggtaaat agttaaagtt atttaaaggt gacgtattgt   2340
tgtaacggtt ttgcatagtt agattaatga aagaaaacga tttaaatcac cttaaatttg   2400
tataccctaa ttattataaa tagataagcc aaagtaaatt tattttaat gataattgac    2460 atatagtcca atagatacct gagttcgtct ttgaagtttg gaatcccat ccgtctcaat    2520 tgcatctaat ttcaacaatt gcatcatcaa caactctatc aataaattaa cttctttctc   2580
ttccaccctc ttcccgtcat taacactacc ttccactgcc gcaacctgca cttaaaaacc   2640
ctaattttat acactcacac tttttgccc ctttccaatt tttttttta aaaaaatgta    2700 taatatgcta gttatccatt ggtcaattca tttcaatcat ttagaattag gttcaattag   2760
aagtttagtc tctaagcttg tttgtaacta tttgttttt aaaccttcta aagcaattca    2820
atgagttatt gaactttcac atttgtctca aataggtttt taaactttag aaatgttacc   2880
taataaccat tttttctttt caaatgtttt cattttgtt acataaacat ttgtatcatt    2940
atcaaaactt cattaaataa aataaaataa agcaaggca tttaaaacta cttttttctt    3000 tttttgtca atttccagaa aaacttgttg tttaaaaaaa aattcacttg agaattcaaa    3060
```

```
tatcttaaaa gtatgtgaat atcataataa ataaatttaat taatttttta      3120 gttataaaat tgaattttag gtgtgaactt aaaaaattta tgaaataaat tattacccat   3180
ttattaaaca caaatgtta gagaaattaa gaatttaaaa acataaacca taccaaccaa   3240
aaaatatcct agacaaatgg taaaaattga ccttaaagta tgataatagt tataacttgc   3300
aattccacct cttaaatttt tttatggtaa aattgagacc tcaaacttaa gtaataatag  3360
aaatggtaaa aattgtataa gtttgagagt tcaatttta tcattttgag cttcaattct   3420
acaattaaac aaaatttaag agtccaattt taacaataat ataaatttaa agacttaatt  3480
tttaatatta aaagtttgaa ggtataactg taattaccac gagtggtttt tacaattttc  3540
tcaaatatat ttttcgacta aagttgtaat ttaacgattt aacgaacctt tcggagagt   3600 ttatcgacct ccgctctgat ccccgccagt gcttcgcctg cagcagtggt attcttcttc   3660
ttcatctctt gaagcttcct ctctttagta gcaggatctt ccatgagtat gagtttcgac   3720
atgtcgttca caccggccat atgcaaccac tcgtcgttct ccttctcctt cccttttaaac  3780 aacaatctct gttccctcgg ctctaaccct gtctgctgtc gtaaaactgt ctttaaattc  3840
cctgtcccaa acacaaaaat taataattca gtcttcaatt taaaataaaa atcaatctgt  3900
atttcaaaaa aaccccccaaa ttgaaatgat aacataccaa atgtggaatg agaatcgacg  3960
gtgatttgat gacgataaga cccatgagat acgttgattg taatgaaacg ctccgaattt  4020
gaacccgaac ccgacccgac atgtcgtttc tgaacaatca ttccacctgg tcggagctcc  4080
caatctacgt ctcctcttcc atactcttcg ctcctaattt ggcttccttt tgaacaccat   4140
tttttcatct ctcttaccaa acaatttccg tttttctttt tttggctcca aattgaaaaa   4200
aaatggtggt gtgtgttgtg ttggttggtt ggatgatgtg agagtgtgag tgaaatgaaa  4260
gcgaaattat aacaaaagaa gaggggggaga gtgtgtcatt gaagaattat tcctatcagg  4320 tccttttttac gtggttgaca attaatcgtt ccaactttcc ttttttttc ccttttattt     4380 agtctctaaa ctttcaaatt aatttaataa cggcgtgtat tttaattttt ttaattataa  4440 atattttag atataacgaa actgttgaat ccaaacccaa ccggacacta atagatagat   4500
gtgtctaata agttaaactt taaattttgt gtctaataaa tttttaaact tataattttg  4560
tatataataa gtatttgata aattaattca tgagttattt tcaaatataa aaaaattttta 4620 aaatatagca aaatatcata tttatcactg atagattact aacatctata attgtctatt  4680
agtaatagac actggtacat gtctatcaat attgtctatt actaataaac agagacattt  4740
ttctatactt gtaaatattt ctagtagttt tgctatttaa aactactacc cttaattcat  4800
ttgtaattaa cctatttgac ataaaattgg atcttatatc taaagaaacg gtaaagttc   4860 acattatgtt taatagatac atgaatttaa aaggtcaagt tttgttcgat aaccatttca  4920
tttttttttt tttttttga aattaagcat ccctcaattt ccaaattcca aaaacaagct    4980
tttttaaaaa taaaaaaata aataataata aatcttttta gatttcaaaa tttagattga   5040
ttttaaaaaa atatattaaa aaaagtagat aacaaatcaa taaattttga gttagaataa   5100
gtgtttataa ggtcttaaat atatattcaa cgtaaaattg aaaatttaag aatgtattaa   5160
aaactaaaat ctcattaaga cacttaatta aaagttgagg acacctaata gatgtaaaat  5220
ttgaaagtta ataacatgta aacttagcct aaagtttaaa agttaggtta aattagtatg  5280
agacagctac ataatagcga cggagatttt aatgactttt caagtgtcag tggattgatg  5340
aaagggacct tcaaacagtc attacgaaca gcggttggtc ggtcacaact ttaaagttcg  5400
```

```
tgattaaaaa gggaattgta catgtccaac tgtccacatc gtacgacaat tcctttaatt    5460
gggcctttgg cccaagtttt ttgggctttg ctggcccaca tatacccgtg ggcttcttga    5520
ggcctctgat catggcttga acttgatgtg atttaggctc ttggtgggct taataaccca    5580
tgcgatgtcc atggggttgt acttcgtgcc atgatattat tgggcccaag cccatgggtt    5640
ctgatgttcg gctgctatct tagtaatttg aagtatatta ttgttgtaaa tacaacaatg    5700
ttcaaagtat taatatatat aatatatcaa tataatagaa tttatagata taccaaaact    5760
tagatttaac tatcgaagtt tattagtgat agagtctatc ggtaatagaa gtctatgact    5820
tgtaggctta tattacttga aatatatcaa caatagaagt atatcattga tagattggta    5880
tcaatgatag agtttatcat ttactctcta tcatgagtag accctatcaa tgatatgagg    5940
tatcaccaat agcaaattaa aatctatcac ttacatataa gactacttat agatttttat    6000
tatgtacttt taagcttcag tcatagacag tttaagtgca atttagttgt ttctagttct    6060
tctagttact ttgaaaagga tattgtaaca aattactttg aatattttgt tgggttatta    6120
atgaaaggga tgagagaata aaattggagg aaaatggagg gaaacaaaaa ggaaaattat    6180
ttgtttgaaa tctatctttg atagaagaga taaattatat atatatatat atatatatat    6240
atgttagttg tgcaatgtga ttgaaatcta tccatcataa tactctatta ttgatagatt    6300
taggttatga attaaaagta tgttagcgat agaattctaa ctatgaaaaa attataccat    6360
cattataagc caacatgagc atagttcaag tgacataaga cgtagatttt tttcttaaa     6420 aaaagtcaaa agttcgaatc ccacaattat tgtgctaaaa aaatataacg ataaatacta    6480 acaaataat aagagagaga aggaaaatga acttataaaa gtacaaaagt aatattacga     6540
cttttaaaag aatgtaattg taaatagagt gaaaaacttc aaagggattt ttttttattt    6600
tttatattta ctatattttt agaaaatga aatgtaatta atatttttaa aaaattataa     6660
agaagattgg aataatatag agaaaatccc agcttctaaa gaagatttct agacataaaa    6720
aattaaattg tcaaacatca tcatcaataa catctctttt aatagcttga ttgacactat    6780
tggtttataa gaagatttct aatggctcaa atgagattag atatatatca cttgatcaac    6840
ttgacattta tcgaaaaatt ttaaacatta atataacatt gaaaataaaa aaggatgatt    6900
tgacaatcaa tgaagttaga cttttttcatc tatacattga agagcaaatt attaatggaa    6960
caatttcatt tttagaaaaa aaataaaata ttttcaaatt tcattcatca aacaaaatcg    7020
ctatattcat gaaattgtgt tttgaggaca tttaacttgg tctaaaacta tcataatttt    7080
agaaacattt taaaaagaga gggccaatga acataaaaaa aaaaaaagt atatatatat     7140 taaaaaaata aaaaataaaa aattatcccc acttagaaaa acaaataata atgataatga    7200
aatatgaagg gagagaaaag gtttataata agaaatggaa gaaataatta gggttggatt    7260
ccttattggt aattttttct aaaaacatgt agggagaggg gaagggggagt ggtccacaga   7320 aatcattgga aatattagaa aaaagtgcc aggctgccat ttttcacccc ccttatgcct     7380
aaaaatacct tattacaacc cctcactaat cattcattca atcgaaacta ttactcgaca    7440
cattgtacac tccttcctct ttttggtttt ctctctttta attctttaat tgattacatc    7500
aaaggtcaac aatttagttc ccattccttg caattgttag actaaaaaaa tggttcagtt    7560
tgtattctct ccataactat tgtaatattt gaaagaaaaa agtacgtaat aacaattatt    7620
tatatggact gtgatgttat attgtaaacg ttatcttcta aattattaaa cgtatgataa    7680
agcaataatt ttgtctccat caatatgata tcgttaacta tattgcaccg agctcctaa    7740 ataatacctt aattaggata atattcaaat caagaatcct aacttgattg agacttgaaa    7800
```

```
aatcatgtca tcaaattaaa ttcccattgt actaaggggg aaaaaaatgc aattgacata   7860
aaagtttcta taggcatatt attgcaccta ttggctttct tatcattcac taccacacgt   7920
ttgccaaaga catggtgtga aagaggggcc cccttacgat catatcattt ttccacttaa   7980
caaattaaaa ataaatagtt cctcaataga aggaattttt ttttttttcaa tacaataaag   8040 atagaaaaat tcaaaataca gactagtttt tggtcactaa cacattcgta tactcttttt   8100
tggaccttaa gttttacgtt tagttttcat ttggtccata gattttaaag agtttgattt   8160
cagtttagtc cctaaatttc aaaatattac aagtttacca ttgggattta aacttttgttt  8220 caatttggtt cctatgtttg aagacttata tttttaactt agatttatca caaaatactc   8280
acttttagcc tttattgtta attatctatt aatttattta aaagaattaa aattgaataa   8340
gtttcactat ttgtccatta ctatttaaat taattttaaa attttacttc ataattattt   8400
taaattaact aaaaaaatat taactccaaa attattttgg aagtgagtat ttagtgaaat   8460
cttgaaactt agagatgaat ttaaaacaaa aacgaaatga ttaccaaata ggacttaatc   8520
tagtaactac aaaataaata tgggcttcat ttacggccat ttcactttca ctttcttagg   8580
caatatctaa atttatatct cataaatgtc ttttaaaagc taagaaatta tggaagcaat   8640
ggagtggacc accccaaatt aaccattaat ttaaacccat tttcaacgaa atcccatcct   8700
ttccattaaa atgtgaatca atcaatgctt gacaaggaa aaataataat aataataata   8760
ataattattt gttttaaata aaagaaagc gaaaaattga ttggccttga aattggaatt   8820
ttcttgtcat cgatctgttt ttgcccttg tatatatggc gttttttaag gtaagaattt   8880
ctagttttcc tcattttca aaaggtggta acggaaaaaa gtactcatta tgtctttgta   8940
atacaatctt ttccaattcc attctttctt agctttcatt ttcatctcta ttattattt   9000 atttttatttt atttaaatat tattttcata tacgcttcca tttacttatt ctgctttgta   9060
ttagccttat gttctaaatt ttgataatat attattattt ttaatatatt ttcataaaag   9120
aaaatttaag attaaattta cgcaaatgaa agtatatgta ttaaaatgga attatactca   9180
aaatacgtag attaaaatgg tatttcaatg gtcaaattat aaaattgatc cctatgattt   9240
tttgaaaaaa attagaattt agtcctccta accataacga ccaaatttgc aatttaatct   9300 atttaatcc aaaatgttca atttgattct tgaactttca aaatatattt tggttgacaa   9360
ttttggtcca tcaatcttca tttttagtct tttttttttt caaaattta tatcaacgtt   9420 ttgcaaacag ggattaagat ggtcattttc aatgtgttga gtgagaaaat tgagtgaatc   9480
ataagttaat tgtattttat taaattaaaa tagaaaagag atgttaattg aataaacaag   9540
agagagagag agagagagaa ttttgtgagg gcatatagtt atcctaacat ggtctgccta   9600
taataagtaa aagaaaagtt aagaaagggt aaaccataga caaggaacac gttctatcat   9660
taatcacttt ttgtctcgta ttaaacacct tttcaaaatt tatcctacca tcttgatgtt   9720
gatatcaaat accatattta caacaaaccc ttcttctctc tccccttatt atataaataa   9780
atttctcctc tcattttttat cactcactca ctctcaatct ttatctttta attttgtttt   9840
ttctaattaa tggggtttaa aggctttgtt attcgaagct acgaagagag tcaattatca   9900
gataaagctc aagttatgga tcttgaacga agatgtgaaa ttggccaatc aaaacgtgtg   9960
tttctcttca ctgacacttt gggtgacccc atttgtagga tacgtaacag tcccatgtat  10020
aaaatgctgg taatctaatt taattttaat taattgtgtt ttttttatagg ttaattaatt  10080 attaatttgt gaattgaaaa ttttttatta ttaaggttgc tgagcgggac aaggaagtgg  10140
```

```
ttggtgttat tcaaggctct ataaaaccgg ttttttttac tgctcataaa ccgccgcccg   10200
gtttggtggt taaactgggc tacattcttg gcctgagagt ggcaccgccg tatcgccgcc   10260
gtggaattgg ctctagcctc gtccgccgtt tggaagattg gttcctttct aatgatgttg   10320
attactgttg tatggccact gagaaagata atcatgcctc tcttaatctc ttcatcaata   10380
atttgaggta ttttccattt ttttcttttt cttttaagtc aacaattatg aattgggaga   10440
gagcacggat cgaacaatca tttttaaaat ggtaattagt gtcattttat cttatgtgtt   10500
atactcagat tagctattaa ctctatctta taatgtaggt tttgtcagta ttttgagaac   10560
tttcaaattt gtgtctaact agttttttt tccttagtta cttaccaaac acgtgataat   10620
attattatat gatgaaattt tttattttt ttattttttt atttattttt tattgtggca   10680
agtaggagca tcatacttac caacaactta atagatataa aattaaaaat ttaatggtca   10740
aatcaaactt tttcgagagt aattttaatg ttgagttttg cacttttaaa tataatttac   10800
gtatgatttt gaaggattag attcatgttt agtttgaagt ggtttagaat ctggcaaaag   10860
ggattttaac aatttcaaac taacgcctct catatttgta gtttgggacg tcactttgct   10920
attaattaac aaaatcacat ttttggaaat taacatatga ttcacatgca actcgtaaat   10980
gaagttaaac ttgaaagttt agaggcatat tagaaatttc tttaaatatt cttttcccca   11040
acaggtacat aaagtttaga acaggaagga tcttggtaaa cccagtaaga aatcatccat   11100
acaatatgaa ttcatcagaa atcaacattc aaaagctaaa aatagaagaa gcagaagcaa   11160
tatacaaaaa acacatggct tcaacagagt tcttccccaa agacataaaa aacatattga   11220
aaaacaagtt gagtttaggg acatgggtgg caaatttcaa acaaccgcca tggtcgtcgt   11280
cgaactctgt tggaggaaac gggcagacta tggcgagtag ctgggccatt gtaagtctat   11340
ggaacagtgg ggaagttttc aagctaaggc taggaaaagc accatttcca tggcttatct   11400
acacaaagag tttaaaaatt atggataaaa ttttccttg ctttaaagtg gttttggtgc   11460
ctaatttttt caagccattt gggttctatt ttgtttatgg attgcaccat gaaggcccctt   11520 tttctgagag attggttgga gctttgtgca aatttgtgca caatatggca ttgaataatt   11580
caaaggataa ttgtaaagct attgttactg agattggagg tgatgaggat gatgggctga   11640
aaatggagat tcctcattgg aaattgctat catgttatga agattttgg tgcataaagt   11700 ccttgaaaag taagagatat aataatatta gtaatgataa tgataacgat aacgatcacg   11760
atcatcatat attggaatgg acaaatgcct cacctaatag aactctcttt gtagacccaa   11820
gagaggtata aaagaataaa aagaaaatag gtttaaccct ctctcgatat gtctcaatct   11880
aattattgtt tgtacttgat agcagagtga agaaagtaga agaaagtta taagaaaga   11940 agaagacgat ttcgatctga actgaaatag ttatgttgta aaattttgtt ttttttgta   12000 cgtggatgtt tctggattta actaggtctc tattcgtatt attgtattca tgactaaata   12060
tgaatgcaaa aaatatcaac gtcgttttct attaatagta tatgtactat tgctttggag   12120
tccaaataat taataatcaa acgataatgt taattctttt gtggattgaa atgtctagat   12180
tttgcatctt attattatgt tttttgtgt gtcatttaag agaaaaaaac ctttagacat   12240
tcctaattta ggtgtcaccc atcttttac tttataaaga ttcaaagttg aaaacaata   12300 agaggagagg catttgggga atattctcat cacatgtgct atatgcaaag gcaataataa   12360
gagtgaaaaa aagaaagat atacataa atagagatta ggttaaatat tgagtgttga   12420
gcttaaaaaa ggtgagagtt tggaattatt agggtttaaa ggaaggccag gtgggggaag   12480
ggcaaagggc aaaaagggga gagatttgag aaaaaagata aagaggagag ttttggaata   12540
```

```
tattattatt agggctttta aaaaacacag ccatggatga gttaggccaa aactttattc    12600
ttcctaaaat ggaaatatgt ctttgcaatt tatggacaat gtgaagttga tttgaagtgt    12660
ttatttgttt atgaaatttt gatggttaat taattataca catacaaatt ttccattttt    12720
tgtgtttgat tctcaaatgg ctgctgtttt atttcagctt gcgttgatta cgttatttga    12780
aaacaaactt cttccctctt ggaccacttg aaagagaatt cattcttgtg agaaaaatgc    12840
atttggatta tatattaggg atgtttacga gatggggcgg ggacggaaat gggagatcgc    12900
ctctttctca tttctcaccc ctcgttataa attttgcagg cattagggtg gtattagata    12960
aacgtacatg agttccatct cattgtagga ctggtatggc aaccttaaag gggtgaatag    13020
agtttattaa attaattaaa acttttact acagtgggcc caattaaaca aatcaatata    13080 cttttttgcga gcaagtaact taaacaataa tttcatgcaa ataaattcat cttgaattag    13140
ataataaatt aacactaata ttttatagaa ccctatttga ttcaagaaga ttggtaaagg    13200
atatgtaaag atcaattcaa cccatctaaa taaatcaatg tgtaagcact taatttaagg    13260
aataaatatt gcaattaatt tcatggaata aaatataata acaaattaat tgcaaaaata    13320
aattagaaga cgtagagagg aaattgacac attttatagt agtttgacac tacccgacct    13380
acatccactc cctaagtttc tcttggatat ggtcactcaa actcgattca ttccacagct    13440
tgaggtgaac tgctacaacg ttcttttttcc aggcacaaga ataaactcga tgttttccac    13500
cattgatgat caaattgtta ccacactctt ctcacaggtt caagagtaac cacttacaat    13560
atgaatttga aaatgaagaa caagatgaga aaaactcttt aaagaagtag gattcacaaa    13620
tttgagctta taaaacaaat caattctcac aatacataaa tctctcttaa aaataagatg    13680
aaaaaaaaaa tgaagcttga agaaagtaac aatggaagct ttgtattttt tttagagaat    13740
taaaaattat gaaaattgtt gttgaaatgt gaaaaagatg aagagtttca aaagagaata    13800
gtgaaatcca aattcattga gtatttaaat catcctaaag agaatattaa atggtttaga    13860
ttaaaaatta aaaaaaaaaa attcttctac tttaaagtga tctccaacag ctacatgcac    13920 ttttttttttt ttttaattat tattattaat ttttaagtca acta                   13964
```